(12) United States Patent
LePivert et al.

(10) Patent No.: US 8,088,413 B2
(45) Date of Patent: Jan. 3, 2012

(54) METHODS FOR IMPROVED CRYO-CHEMOTHERAPY TISSUE ABLATION

(75) Inventors: Patrick LePivert, Jupiter, FL (US); Dennis R. Morrison, Pensacola, FL (US)

(73) Assignee: Nuvue Therapeutics, Inc., Fairfax, VA (US)

( * ) Notice: Subject to any disclaimer, the term of this patent is extended or adjusted under 35 U.S.C. 154(b) by 305 days.

(21) Appl. No.: 12/212,421

(22) Filed: Sep. 17, 2008

(65) Prior Publication Data

US 2009/0011032 A1   Jan. 8, 2009

Related U.S. Application Data

(63) Continuation-in-part of application No. 11/097,991, filed on Mar. 31, 2005, now Pat. No. 7,833,187.

(60) Provisional application No. 60/562,759, filed on Apr. 16, 2004.

(51) Int. Cl.
*A61K 9/16* (2006.01)
(52) U.S. Cl. .................................. 424/490; 604/507
(58) Field of Classification Search .................. 424/490; 514/12, 274, 449; 604/507
See application file for complete search history.

(56) References Cited

U.S. PATENT DOCUMENTS

| | | | |
|---|---|---|---|
| 5,329,927 A | 7/1994 | Gardineer et al. | |
| 5,425,370 A | 6/1995 | Vilkomerson | |
| 5,827,531 A | 10/1998 | Morrison et al. | |
| 5,862,672 A * | 1/1999 | Faries et al. | 62/68 |
| 6,235,018 B1 | 5/2001 | LePivert | |
| 6,623,430 B1 | 9/2003 | Slayton et al. | |
| 6,788,977 B2 | 9/2004 | Fenn et al. | |
| 6,803,052 B2 | 10/2004 | Faisant et al. | |
| 6,918,869 B2 * | 7/2005 | Shaw et al. | 600/3 |
| 6,931,026 B1 * | 8/2005 | Lee et al. | 370/468 |
| 2003/0039613 A1 * | 2/2003 | Unger et al. | 424/9.51 |
| 2004/0106841 A1 * | 6/2004 | Shaw et al. | 600/3 |
| 2005/0227910 A1 * | 10/2005 | Yang et al. | 514/2 |
| 2008/0208052 A1 | 8/2008 | LePivert | |
| 2009/0125087 A1 * | 5/2009 | Becker et al. | 607/113 |
| 2009/0301107 A1 * | 12/2009 | Kammer et al. | 62/68 |
| 2009/0326621 A1 * | 12/2009 | El-Galley | 607/105 |

FOREIGN PATENT DOCUMENTS

WO   WO2006095330   9/2006

OTHER PUBLICATIONS

J. Joosten et al, "In vivo destruction of tumor tissue by cryoablation can induce inhibition of secondary tumor growth: an experimental study", Cryobiology, 41:49-58 (2001).
Jaattela M., Escaping cell death: survival proteins in cancer. Exp Cell Res. (1999), pp. 30-43, 248 (1).

(Continued)

*Primary Examiner* — Nicholas D Lucchesi
*Assistant Examiner* — Gerald Landry, II
(74) *Attorney, Agent, or Firm* — McHale & Slavin, P.A.

(57) ABSTRACT

The current invention relates to a process for increasing the efficacy of cancerous disease inhibiting therapeutic agents delivered to a treatment region of a tissue structure, such as a tumor. The multi-step procedure takes advantage of the resulting thermal stress response occurring as a result of exposure to the cold. Coordinating the thermal related stress response with the timing of cancerous disease inhibiting agent action provides a unique therapeutic regiment to treat tumors which provides a maximized effect on the tumor, protects normal cells, and activates local pro-inflammatory cells.

40 Claims, 7 Drawing Sheets

OTHER PUBLICATIONS

De Meester SL, Buchman TG, and Cobb JP. The heat shock paradox: does NF-•Bdetermine cell fate? (2001) pp. 270-274, FASEB J 15.

Curry HA, Clemens RA, Shah S, Bradbury CM, Botero A, Goswami P, and Gius D. Heat shock inhibits radiation-induced activation of NF-kB via inhibition of I-B kinase. J Biol Chem (1999) pp. 23061-23067, vol. 274.

Yoo CG, Lee S, Lee CT, Kim YW, Han SK, and Shim YS. Anti-inflammatory effect of heat shock protein induction is related to stabilization of I-B through preventing I-B. activation in respiratory epithelial cells, J Immunol (2000) pp. 5416-5423, vol. 164.

Feinstein DL, Galea E, Aquino DA, Li GC, Xu H, and Reis DJ. Heat shock protein 70 suppresses astroglial-inducible nitric-oxide synthase expression by decreasing NF-kB activation. J Biol Chem (1996) pp. 17724-17732, vol. 271.

Scarim AL, Heitmeier MR, and Corbett JA. Heat shock inhibits cytokine-induced nitric oxide synthase expression by rat and human islets. Endocrinology, (1998) pp. 5050-5057, vol. 139.

Ohnishi T, Wang X, Ohnishi K, Matsumoto H, and Takahashi A. p53-dependent induction of WAF1 by heat treatment in human glioblastoma cells. J Biol Chem (1996) pp. 14510-14513, vol. 271.

Nitta M, Okamura H, Aizawa S, and Yamaizumi M. Heat shock induces transient p53-dependent cell cycle arrest at G1/S. Oncogene (1997) pp. 561-568, vol. 15.

Ayad O, Stark JM, Fiedler MM, Menendez IY, Ryan MA, and Wong HR. The heat shock response inhibits RANTES gene expression in cultured human lung epithelium. J Immunol (1998) pp. 2594-2599, vol. 161.

Fujita J. Cold shock response in mammalian cells. J. Mol. Microbiol. Biotechnol. (1999) pp. 243-255, vol. 1.

Gon Y, Hashimoto S, Matsumoto K, Nakayama T, Takeshita I, and Horie T. Cooling and rewarming-induced IL-8 expression in human bronchial epithelial cells through p38 MAP kinase-dependent pathway. Biochem Biophys Res Commun (1998) pp. 156-160, vol. 249.

Nishiyama H, Itoh K, Kaneko Y, Kishishita M, Yoshida O, and Fujita J. A glycine-rich RNA-binding protein mediating cold-inducible suppression of mammalian cell growth. J Cell Biol (1997) pp. 899-908, vol. 137.

Matijasevic Z, Snyder JE, and Ludlum DB. Hypothermia causes a reversible, p53-mediated cell cycle arrest in cultured fibroblasts. Oncol Res (1998), pp. 605-610, vol. 10.

Kaneko Y, Nishiyama H, Nonoguchi K, Higashitsuji H, Kishishita M, and Fujita J. A novel hsp110-related gene, apg-1, that is abundantly expressed in the testis responds to a low temperature heat shock rather than the traditional elevated temperatures. J Biol Chem (1997) pp. 640-2645, vol. 272.

Holland DB, Roberts SG, Wood EJ, and Cunliffe WJ. Cold shock induces the synthesis of stress proteins in human keratinocytes. J Invest Dermatol (1993) pp. 196-199, vol. 101.

Ohnishi T, Wang X, Ohnishi K, and Takashi A. p53Dependent induction of WAF1 by cold shock in human glioblastoma cells. Oncogene (1998) pp. 1507-1511, vol. 16.

Nishiyama H, Danno S, Kaneko Y, Itoh K, Yokoi H, Fukumoto M, Okuno H, Millan JL, Matsuda T, Yoshida O, and Fujita J. Decreased expression of cold-inducible RNA-binding protein (CIRP) in male germ cells at elevated temperature. Am J Pathol (1998) pp. 289-296, vol. 152.

Ars E, Serra E, de la Luna S, Estivill X, and Lazaro C. Cold shock induces the insertion of a cryptic exon in the neurofibromatosis type 1 (NF1) mRNA. Nucleic Acids Res (2000), pp. 1307-1312, vol. 28.

Hanai A, Yang WL, Ravikumar TS. Induction of apoptosis in human colon carcinoma cells HT29 by sublethal cryo-injury: mediation by cytochrome c release. Int J Cancer. Aug. 15, 2001;pp. 526-533, vol. 93(4).

Forest V, Peoc'H M, Ardiet C, Campos L, Guyotat D, Vergnon JM. In vivo cryochemotherapy of a human lung cancer model. Cryobiology. (2005), pp. 92-101, vol. 51(1).

Grand RJ, Milner AE, Mustoe T, Johnson GD, Owen D, Grant ML, and Gregory CD. A novel protein expressed in mammalian cells undergoing apoptosis. Exp Cell Res (1995), pp. 439-451, vol. 218.

Clarke DM, Baust JM, Van Buskirk RG, Baust JG., Addition of anticancer agents enhances freezing-induced prostate cancer cell death: implications of mitochondrial involvement. Cryobiology. (2004) pp. 45-61, vol. 49(1).

Gyrd-Hansen M, Nylandsted J, Jaattela M. Heat shock protein 70 promotes cancer cell viability by safeguarding lysosomal integrity, Cell Cycle. Dec. 2004;pp. 184-185, vol.3(12).

Chappel SA, Owens GC, and Mauro VP. A5. leader of Rbm3, a cold stress-induced mRNA, mediates internal initiation of translation with increased efficiency under conditions of mild hypothermia. J Biol Chem (2001) pp. 36917-36922,vol. 276.

Danno S, Itoh K, Matsuda T, and Fujita J. Decreased expression of mouse Rbm3, a cold-shock protein, in Sertoli cells of cryptorchid testis. Am J Pathol (2000) pp. 1685-1692, vol. 156.

Danno, S, Nishiyama, H, Higashitsuji ,H, Yokoi H, Xue, JH, Itoh K, Matsuda T, and Fujita J. Increased transcript level of RBM3, a member of the glycine-rich RNA-binding protein family, in human cells in response to cold stress. Biochem Biophys, Res Commun(1997) pp. 804-807, vol. 236.

Ohsaka Y, Ohgiya S, Hoshino T, and Ishizaki K. Mitochondrial genome-encoded ATPase subunit 6 8 mRNA increases in human hepatoblastoma cells in response to nonfatal cold stress. Cryobiology (2000), pp. 92-101, vol. 40.

Chao, B. H., Bischof, JC. Pre-treatment inflammation induced by TNF-alpha augments cryosurgery injury on human prostate cancer, Cryobiology (2004) pp. 10-27, vol. 49(1).

Sonna, LA, Kuhlmeier, MM, Carter HC, Hasday, JD, Lilly CM, and Fairchild, KD. Effect of moderate hypothermia on gene expression by THP-1 cells: a DNA microarray study. Physiol. Genomics (2006), pp. 91-98, vol. 26(1).

Wang H, Wang H, Zhang W, Huang HJ, Liao WS, Fuller GN. Analysis of the activation status of Akt, NFkappaB, and Stat3 in human diffuse gliomas. Lab Invest. (2004) pp. 941-951, vol. 84(8).

Clarke, D.M., Baust, J.M., Van Buskirk, R.G., Baust, J.G. Chemo-Cryo Combination Therapy: An Adjunctive Model for the Treatment of Prostate Cancer. Cryobiology. (2001) pp. 274-285, vol. 42.

Mir L.M., Rubinski, B., Treatment of Cancer with Cryochemotherapy. British Journal of cancer (2002), pp. 1658-1660, vol. 86.

Katz, A and Rewcastle J. The current and Potential Role of Cryoablation As a Primary Therapy for Localized Prostate Cancer, Current Oncology Reports (2003) pp. 231-238, vol. 5.

Onik G. Image-Guided Prostate Cryosurgery: State of the Art, Cancer Control (2001) pp. 522-531, vol. 8(6).

Tian-Hua Yu, Jingliu, Yi-Xin Zhou. Selective freezing of target biological tissues after injection of solutions with specific thermal properties. Cryobiology, (2005) pp. 50, 2, 174-182.

Han,B., Ifftekhar, A., Bischoff, J. Improved cryosurgery by use of thermophysical and anti-inflammatory adjuvants. TCRT,(2004) p. 3,103-111.

Nishiyama, H et al. A glycine-rich RNA—binding protein mediating cold-inducible suppression of mammalian cell gorwth, J Cell Biol, (1997) pp. 899-908; vol. 137.

Kaneko, Y, et al. A novel hsp110-related gene, apg-1, that is abundantly expressed in the testis responds to a low temperature heat shock rather than the traditional elevated temperatures. J Biol Chem (1997) pp. 2640-2645, vol. 272.

De La Taille, et al. Cryoablation for clinically localized prostate cancer using an argon-based system: complication rates and biochemical recurrence. BJU (2000) pp. 281-286, vol. 85(3).

Patrick J. Le Pivert, MD., Dennis R. Morrison, PhD., Ruwaida S. Haddad, PhD, Jacques Doulat, PhD, Michel Renard,PhD, Alex Aller, PhD, and Kerry Titus, BS. Percutaneous Tumor Ablation: Microencapsulated echo-quided Interstitial Chemotherapy Combined with Cryosurgery Increases Necrosis in Prostate cancer (2008).

Patrick J. Le Pivert, Ruwaida S. Haddad, Alex Aller, Kerry Tutus, Jacques Doulat, Michel Renard and Dennis R. Morrison Ultrasound Guided, Combined Cryoablation and Microencapsulated 5-Fluorouracil, Inhibits Growth of Human Prostate Tumors in Xenogenic Mous Model Assessed by Luminescence Imaging, Technology in Cancer Research & Treatment, (2004) pp. 135-142, vol. 3(2).

* cited by examiner

| TREATMENT | | N | TUMOR RADIUS (mm) | NECROSIS RADIUS (mm) | DAY 3 IB KILL RATIO |
|---|---|---|---|---|---|
| COMBINATION (CA+MCC/5-FU) | Mean S.D. | 11 | 6 1 | 3.8 0.3 | 0.54 0.12 |
| CRYO (CA) | Mean S.D. | 12 | 4.7 0.9 | 3.1 0.6 | 0.40 0.9 |

*FIG 3A*

| Treatment (A549.Dec.2004) | No. Tumors Treated | No. Tumors Cured | Day of Cure | Percent cure at 3 weeks |
|---|---|---|---|---|
| Combined Therapy (cryo+5FU) | 16 | 4 | 11 to 14 | 25% |
| µcaps Chemo (5FU) | 16 | 0 | | 0% |

*FIG. 3B*

METHODS FOR IMPROVED CRYO-CHEMOTHERAPY TISSUE ABLATION

CROSS REFERENCE TO RELATED APPLICATION

This application is a continuation-in-part of and claims priority under 35 U.S.C. § 120 to U.S. patent application Ser. No. 11/097,991, filed on Mar. 31, 2005 now U.S. Pat. No. 7,833,187, which claims the benefits to U.S. Provisional Application 60/562,759, filed on Apr. 16, 2004 under 35 U.S.C. § 120, the contents of each are herein incorporated by reference.

FIELD OF THE INVENTION

This invention relates to the field of treatment of tumors; more specifically to improved treatments using a combination cryosurgery (cryoablation) and injection of tumor inhibiting substances which provides a maximized effect on the tumor, protects normal cells, and activates local pro-inflammatory cells.

BACKGROUND OF THE INVENTION

Percutaneous image-guided cryosurgery has become an alternative Minimally Invasive Surgical (MIS) modality for the focal treatment of certain cancers, such as prostate cancer (Katz, A and Rewcastle, J. The current and Potential Role of Cryoablation As a Primary Therapy for Localized Prostate Cancer, *Current Oncology Reports* 5:231-238, 2003). Use of multiple thin cryoprobes has enabled shaping of the ice balls formed thereof to the prostate lesion and ultrasonographic guidance have yielded better results in terms of local eradication. Investigators have reported good intermediate-term results of cryoablation (CA) when used for salvage in post-radiation patients and for primary cancers (Onik G. Image-Guided Prostate Cryosurgery: State of the Art, *Cancer Control* 8(6):522-531, 2001). When used for those procedures the technique produces outcomes similar to brachytherapy and three dimensional conformational radiotherapy. The main advantages of cryosurgery include the ability to re-treat patients without added morbidity and to treat salvage post-radiation patients with acceptable results and morbidity. Recent publications demonstrate durable efficacy for cryoablation which are equivalent to other therapies for low-risk disease and possibly superior for moderate to high-risk prostate cancer. However, the multi-focal nature of prostate cancer as well as the biochemical recurrence rate associated with salvage post-radiation or primary cryoablation of localized cancers suggests that there are residual patches of untreated tumor cells in a significant number of cases (De La Taille, et al Cryoablation for clinically localized prostate cancer using an argon-based system: complication rates and biochemical recurrence. *BJU* 85(3):281-286, 2000). New focal treatments are needed that can be precisely delivered into tumors that cannot be effectively treated by CA alone.

Combined local therapies, such as cryosurgery and radiation or cryoablation and intratumor injection of cytotoxic drug(s) or chemical adjuvants, i.e. "cryochemotherapy," have become a promising alternative method for physicians attempting to overcome limitations of the current treatment (Han, B, et al. Improved cryosurgery by use of thermophysical and anti-inflammatory adjuvants. *TCRT,* 3,103-111, 2004 and Tian-Hua, Yu, et al. Selective freezing of target biological tissues after injection of solutions with specific thermal properties. Cryobiology, 50, 2, 174-182, 2005). Although results have been inconsistent, cryosurgery has also been associated with systemic chemotherapy to increase its local efficacy. For example, in vitro experiments using a combination of free drug, 5-fluorouracil (5-FU), given for 2 to 4 days prior to freezing of a human prostate cancer cell line, PC3, resulted in an increased kill efficacy of cryoinjury (Clarke, D M, et al Chemo-Cryo Combination Therapy: An Adjunctive Model for the Treatment of Prostate Cancer. *Cryobiology.* 42, 274-285, 2001). Interestingly, the drug and cryosurgical regimen were used at levels individually ineffective. In 2002, scientists reported similar results in vitro with the concomitant use of a single freeze-thaw cycle and free bleomycin on B16 F0 melanoma cells, where the membranes of the frozen cells became more permeable to the drug (Mir, LM and Rubinsky, B. Treatment of Cancer with Cryochemotherapy. *British Journal of cancer* 86, 1658-1660, 2002).

Cryosurgery is recognized as an efficient, thermo-ablative, minimally invasive, method for a large number of solid tumors like prostate, lung, liver, kidney, to cite only a few. Cryosurgery affects tumor tissue viability in three different ways with immediate and delayed alterations: freezing of tumor cells, tumor kill through direct cell alterations, and indirect vascular occlusion. Recently apoptosis, a programmed, gene-regulated cell death, has been shown predominant at the margins of a cryolesion, both at freezing and sub-freezing temperatures and is thought to be another mechanism of cellular killing consecutive to cryothermal changes.

To achieve cryoablation, the entire tumor must be frozen to "kill" temperatures in the range of −40° C. The Freeze/Thaw (F/T) cycle must be repeated, and the kill temperature, out to the tumor margins, must be maintained for a few minutes, and designated as "hold time," during cryosurgery. Despite a strict adherence to these time-consuming standards, certain tumors like prostate or metastatic liver cancer show a 20 to 40% post-procedure recurrence. Whether the cause of this failure is disease-based or technique-related, it is recognized that cryosurgery needs the support of adjunctive therapy in the form of chemo- or radiotherapy to increase the rate of cell death at margins of the cryogenic lesion where the cell fate is known to be in balance for several days post treatment.

The pretreatment of a tumor with a pro-inflammatory protein like Tumor Necrosis Factor-alpha, based on the hypothesis that vascular-mediated injury is responsible for defining the edge of the cryolesion in microvascular-perfused tissue, augments the cryoinjury that occurs at much higher temperatures, close to 0° C., due to an inflammatory pre-sensitization of the microvasculature (Chao, BH and Bischof, JC. Pre-treatment inflammation induced by TNF-alpha augments cryosurgery injury on human prostate cancer, *Cryobiology* 49(1):10-27, 2004). Although this pretreatment seems better in terms of ablation completeness, it doesn't act directly on tumor cells and particularly on cells that may have escaped the margin of the cryolesion.

Hence there is a clear need for agents, neo-adjuvant or adjuvant to cryosurgery that could increase the cryosurgical kill as well as the tumor cell kill within and outside the frozen region, while sparing the normal cells and tissue structures.

Systemic chemotherapy has long been used to enhance the kill effect of cryosurgery on experimental and human solid tumors, but results have been inconsistent. This inconsistency could be the result of the fact that combined treatments were not based on sound protocols defining the drug, dosages, route of administration and timing of applications. Since most common chemotherapeutic drugs initiate apoptosis in cancer cells, and given that a similar effect is observed with sub-freezing temperatures, the timely conjunction of each method has been sought for optimizing tumor cell death at tumor margin.

Several papers have shown that in vitro moderate freezing temperatures combined with low dose chemotherapy increased the rate of cell death for prostate and colo-rectal cancer cells. However, these findings were not transferred to in vivo experiments. Several drawbacks associated with using systemic chemotherapy include unpreventable side effects, intermittent tumor exposure to therapeutic doses, and unpredictable tumor penetration. Moreover, tumor cells need to be frozen which increases the risk of damage to neighboring normal tissue by excessive freezing. The cytotoxic drug penetration into the tumor may be difficult and imprecise upon initiation of cryo-induced microvascular impairments particularly if a precise timing between the drug administration and the cryo-application has not been properly coordinated. The drug properties are also critical and should be selected on the basis of their ability to act on the tumor cells as well as on the microvascular network constituents.

There is a need for a more effective cryochemotherapy combination that would increase the tumor cell kill both in the frozen and unfrozen regions of the cryo-application and expose the cells and/or the microvascular bed to effective concentrations of drug for longer durations, while preventing systemic adverse effects.

Intra-tumor chemotherapy using different drugs and vectors or carriers of those drugs has been proposed to improve local delivery of chemotherapeutic agents and to decrease their side effects. These new formulations, such as microspheres, liposomes, and matrixes, have the capability of slowly releasing the active component at therapeutic dose by diffusion through membrane and/or progressive degradation/lysis at body temperature. Such sustained release exposes cells to higher concentration of the cytotoxic drug for longer periods of time, prevents side effects, and results in better outcome. Drug carriers deposited locally or into the vascular bed of the tumor as the sole treatment and/or as a pre-adjuvant or adjuvant therapy to surgical excision, radiation therapy, 5-FU encapsulation and glioblastomas, are taught in U.S. Pat. No. 6,803,052, or microwave hyperthermia, as taught in U.S. Pat. No. 6,788,977 and U.S. Pat. No. 6,623,430. For the latter, moderate hyperthermia of the target organ is triggering the release of the drug out of the thermo-sensitive, solid-matrix microsphere containing doxorubicin, THERMODOX. For safety and efficacy, these treatments rely on the precise, homogeneous deposition and known degradation rates of the carriers. Since these carriers can not be imaged, there is no method to determine, in real time, the optimum delivery, in terms of spatial distribution, and dose. Such assessments are based only on direct visualization during open surgery and on indirect measurement of tissue temperature.

Cryosurgery has been associated with curettage and topical chemotherapy with 5-FU for the treatment of actinic keratosis (AK), a pre-cancerous lesion that usually does not metastasize. One of the topical ointments CARAC CREAM contains 0.5% fluorouracil, with 0.35% incorporated into a patented porous microsphere, MICROSPONGE, composed of methyl metacrylate. However, the prescribed mode of application does not call for a specific geometric deposition of the cream, i.e. preferentially at lesion margins, or timing between cryoablation and chemoablation. As a result, the method is not optimized to increase the cryo-kill at warmer temperatures nor does it spare the neighboring normal skin.

Various drug mixtures and carriers containing cytotoxic agents have also been injected directly into the vascular bed of tumor through selective or supra-selective catheterization with adapted instruments. The combination of cytotoxic drug with agents of embolization is used to increase the cell death rate by submitting the tumor cells to elevated drug concentrations and ischemia consecutive to microvascular thrombosis. However, embolization techniques are not easy. They require specific and costly technologies, highly specialized departments, and the drug distribution is not necessarily homogeneous.

A major drawback of the sustained-release drug carriers, such as delivery carriers like microspheres, liposomes, microcapsules, and gel-foam particles, is that they are not continuously visible using most of the available real-time visible clinical imaging systems, i.e. ultrasound imaging, C-T radiography or fluoroscopy. As a consequence, the physician is unaware if the desired target site of deposition has been reached or if the drug carriers are correctly distributed throughout the tumor or target tissues. To compensate for this drawback, mixtures or emulsions of insoluble contrast agents, like ETHIODOL carriers, have been mixed with the drug solutions or carriers just prior to administration. However since the carrier and the contrast agent diffusion/distributions in tissues are different, the imaging of the contrast in the mixture does not give a precise location of the carrier beyond a short period of time. A further drawback is that pinpoint placement of the depots into the tumor requires the surgeon to have unobstructed views of the delivery device until the delivery tip reaches the targeted tumor region, particularly for deep-seated lesions. Although a number of techniques have been described to increase the echogenicity of delivery needles or catheters during various procedures, their characteristics are not helpful for visualization in deep-seated lesions, where their effectiveness would be most desirable.

Drug release from biodegradable carriers is an important aspect of its use. Common methods include spontaneous release at core body temperature by matrix degradation or diffusion outward from matrix spheres and substrates. For most of these carriers drug release is slow and cyclic which lowers anti-tumor efficacy. Controlled release aims at increasing effectiveness of the drug by immediate and/or sustained release of a large volume of the drug. It prevents complications, such as embolization, from carriers that have unwillingly moved to unwanted location, and allowing for combined technologies that sensitize tumor cells by increasing their permeability to the drug.

Finally, since the cellular heterogeneity of malignant tumors is one of the major factors that explain tumor resistance to an initially effective single drug chemotherapy it would be an advantage to encapsulate a mixture of drugs that would overcome this chemo-resistance. Currently available sustained release systems encapsulate only a single drug.

There is a need for a minimally invasive, combined cryoablation method that would simultaneously expose the periphery of a tumor to effective concentrations of agents for longer durations while preventing systemic adverse effects and preventing further damage to normal healthy tissues. Such a method would enhance safety and efficacy of cryoablation with injection of cancerous disease inhibiting therapeutic agent.

DESCRIPTION OF THE PRIOR ART

This invention incorporates and improves on the subject matter of several patents: e.g., U.S. Pat. No. 6,235,018 for monitoring cryosurgery; U.S. Pat. No. 5,425,370 that oscillates the delivery device(s) at its resonant frequency; and U.S. Pat. No. 5,827,531 that discloses the unique microcapsules. All of these patents are incorporated herein by reference. The patent material is summarized below for a clear understanding of the objects and advantages of the present invention.

The computer-aided monitoring method disclosed in U.S. Pat. No. 6,235,018 predicts, in real-time, the extent of the ice ball kill zone, and, alone, or in conjunction with conventional imaging techniques, such as, Ultrasound, "US", Computerized Tomography, "CT", Magnetic Resonance, "MR" allows a precise location of the target regions for complementary treatment with unique imageable drug(s) carriers.

Microcapsule based drug delivery systems are based on (1) microcapsules originally found in U.S. Pat. No. 5,827,531, later modified to make them echogenic using one or more dense contrast imaging agents adapted to various imaging modalities co-encapsulated with the drug(s) solution; (2)) 98% payload volume of the microballoon type of microcapsules is a shared composition of drug and contrast; typically 60-88% drug co-encapsulated with 40-12% contrast agent; (3) multiple drugs in single microcapsules; and (4) microcapsules with selected thermosensitivity of the outer membrane which allows slow lysis of the microcapsules after they are deposited in the body and thereby sustained, bulk, release of the therapeutic agents contained therein.

The precise deposition of the imageable drug(s) carriers is made possible in superficial as well as in deep-seated tissues with a vibrating delivery device(s) of U.S. Pat. Nos. 5,425,370 and 5,329,927. This device allows for the pinpoint delivery and continuous, accurate visualization of minimally invasive, indwelling diagnostic needles and therapeutic probes and catheters in real-time, via the use of resonant frequency Ultrasound, which allows for the positioning, interstitially, of these devices into targeted tissue regions via direct, minimally invasive, endoluminal, and/or endovascular (intra-arterial or intravenous) approaches. The spatial deposition of carriers is into and preferably at tumor margins. The latter must coincide with thermal margins of ice ball; the deposition is followed by a controlled release of drug(s), from through-wall diffusion and/or vector degradation, with adapted needle(s), catheter(s), and/or probe(s). Ultrasound imaging allows for real-time visualization and most effective loading of tumor tissue with the carriers as well as their degradation, which corresponds to the disappearance of their ultrasonic image.

In our previous application, U.S. patent application Ser. No. 11/097,991, the concurrent use of cryosurgery and local concurrent delivery of small doses of cytotoxic drugs off biodegradable microcapsule deposits within selected sites (i.e. unfrozen region that is peripheral to the frozen margin of the cryolesion) of the cryosurgically treated tumor for an improved tumor ablation (cryochemoablation) was disclosed. The combined local action of the sustained drug concentration and the cooling stress on the tumor cells lead to an unexpected synergistic kill effect (necrosis and cryonecrosis) that was superior to that of each individual element when used individually. Whereas the one-time hypothermic stress was transient and non-lethal, the selected drug was released by its polymeric carrier at a concentration that was also insufficient for a complete kill. In addition, 5-fluorouracil (5-FU) was thought previously to have little anti-tumor activity on the selected human prostate and lung tumors.

Nevertheless the combined action of the sub-lethal stressors leads to a significant increase of the distance of necrotic kill (cryonecrosis) from the cryoprobe in the direction of the microcapsule deposits (directional kill). It is assumed that the minute amount of cancerous disease inhibiting therapeutic agent delivered from the microcapsule carrier at time of tissue deposition as well as during the following days (from microcapsule lysis and drug diffusion through membrane) is adding its deleterious effect to the thermally stressed tumor cells (suprazero thermal stress at about +12 degrees Celsius (° C.), or between 0.56° C. to +22° C.) as well as to the endothelial cells of the microvascular network. It is assumed that the thermal stress from the transient hypothermia sensitizes tumor cells and vasculature to the cytotoxic, apoptotic, and anti-angiogenic stress of the sub-toxic sustained dose of the cancerous disease inhibiting therapeutic agent on the same targets. Such spatially targeted and timely deposition of the cancerous disease inhibiting therapeutic agent may increase the safety and effectiveness of cryoablation for pathologic conditions such as hormone refractory prostate cancer or non-small cell lung (NSCL) cancer on human patients.

To date, no studies have described using local deposition of vascular-affinity non-specific substances or drugs in a region of cryosurgically induced mild and transient focal hypothermia to enhance drug retention. Moreover, no studies have described the effects on the tumor microvascular network resulting from the local deposition of vascular-affinity non-specific substances or drugs in a region of cryosurgically induced mild and transient focal hypothermia with the goal of eliminating the microvascular network. Therefore, what is needed is improved treatments using hypothermic treatment and injection of cancerous disease inhibiting therapeutic agents.

SUMMARY OF THE INVENTION

The current invention relates to a process for increasing the efficacy of cancerous disease inhibiting therapeutic agents delivered to a treatment region of a tissue structure, such as a tumor. The process involves freezing a designated treatment area within a treatment structure. Freezing of the tissue results in the formation of several thermal regions and induces the thermal stress response. Coordinating the thermal related stress response with cancerous disease inhibiting therapeutic agent drug action provides a unique therapeutic regimen to treat tumors which provides a maximized effect on the tumor, protects normal cells, and activates local pro-inflammatory cells.

The process involves freezing a designated treatment area within a treatment structure. Freezing of the tissue results in the formation of several thermal regions and induces the thermal stress response. The thermal related stress response has one or more of the following effects, an immediate or delayed cellular kill, increase vascular stasis or thrombosis, increase medium viscosity, increase interstitial pressure, increase cryoporation, increase cryophoresis, increase tumor tissue chemosensitivity, an increase protection of normal tissue, and increase tumor tissue apoptosis. It is believed that thermally induced changes in conjunction with injection of cancerous disease inhibiting therapeutic agent increases the homogenous cell kill and increase the kill in regions where cells usually escape the thermal kill, such as the margins of the regions and the hypothermal region. Enhanced efficacy provided by the process has the potential to allow delivery of lower amounts of cancerous disease inhibiting therapeutic agents during treatment for various tumors while potentially increasing the kill of standard chemo-ablative procedures.

Once thermal insult, i.e. cryosurgical freezing, has been initiated, injection of cancerous disease inhibiting therapeutic agents upon targeted tissues takes effect immediately through various predominant mechanisms. Since the cancerous disease inhibiting therapeutic agents are injected into a specific region, the proper concentration is achieved rapidly. Unlike systemic routes, cancerous disease inhibiting therapeutic agents interstitially injected within a tumor region act on specific cells and at desired concentrations. Once positioned at the proper region of interest, cancerous disease inhibiting therapeutic agents diffuse to regions of interest. Thermal insult further results in tumor tissues sensitivity to cancerous disease inhibiting therapeutic agents, with cellular thermoporation facilitating drug penetration. The slush region and supra-zero hypothermia regions are upstaging diffusion, poration and retention and it is these regions which are preferentially targeted for injection of cancerous disease inhibiting therapeutic agents.

For injection of cancerous disease inhibiting therapeutic agents to have a delayed effect, starting at 24-48 hours, on ice kill and similar thermal insult, several mechanisms are proposed. First, thermal sensitization of tumor tissue results through increased p53 and cycling tumor tissue lacking p53 expression. Programmed cell death, or apoptosis, is triggered through hypo-thermal induction of cold stress proteins (HSPs, class HSP-90, HSP-70) and pro-apoptotic signaling proteins (such as caspase-3, caspase-9, bcl-2) that produce a net result of increased apoptosis in tumor cells and inhibited cell cycle progression (protection) in normal cells. Cancerous disease inhibiting therapeutic agents are retained within the injection site and preferentially diffuse to zones of drainages, such as microvascular networks. To take advantage of such actions, cancerous disease inhibiting therapeutic agent encapsulated within microcapsules are within the scope of the invention, allowing time release of such agents to the areas of interest.

Placement of cancerous disease inhibiting therapeutic agent in any one of the regions offers unique advantages to treating cancerous tumors that have not been previously disclosed. Although injection into any region is contemplated, a preferred embodiment includes injection within the supra-zero hypothermia region. Moreover, injection of the cancerous disease inhibiting agents may be injected prior to, subsequent to, or concurrently with freezing of the tissue structure.

In accordance with this invention, "cancerous (or cancer) disease inhibiting" or "CDI" is understood to mean any substance that is cytotoxic, tumor inhibiting and/or vascular/microvascular acting to the tumor. Interference with the tumor metabolism and/or interruption of the microvascular/vascular flow of tumor is also included in this definition.

In accordance with this invention, "cancerous (cancer) disease inhibiting therapeutic agent(s)," "CDI-therapeutic agent(s)," or "therapeutic agent(s)" may be used interchangeably and is understood to mean one or more free drugs and/or substances and/or encapsulated drugs or substances which are cytotoxic, tumor inhibiting, and/or have an affinity for the tumor vascular network rather than tumor cells which can be used in combination with localized tumor hypothermia to induce tumor necrosis and/or inhibition of tumor growth or substances that work on tumor cells.

Given the wide array of compounds which may be used for the combined therapy and/or based on the nature and type of tumor, it can be appreciated by one of skill in the art that any free substance, drug, chemical, or combinations thereof, including, but not limited to, sclerosant, cytotoxic drug(s), cytostatic drug(s), cytolytic drug(s), antiangiogenic, immune stimulants, immune suppressants, drugs which effect the immune system, cytokines, immunostimulatory cytokines, anti-cancer drugs, and other materials are contemplated within the invention. Illustrated examples include polyethylene glycol (PEG), dextran, glycerol monostearate, 5-fluorouracil (5-FU), paclitaxel, methotrexate, Ethiodol, individually or in combination with substances listed above, and microcapsules and microcapsule debris, including membrane components, oily contrast agents, and other materials.

In accordance with this invention, "freeze region" is understood to mean any area of the tumor that has a temperature of less than $0°$ C.

In accordance with this invention, the term "ice ball" includes the area formed around a cryoprobe upon freezing. The ice ball region is made up of two thermal zones, the hard ice region and the slush ice region.

In accordance with this invention, "hard ice region" is defined to mean the first region which defines the ice ball and forms closest to the cryoprobe tip. This region is defined by tissue temperatures less than minus $21°$ C.

In accordance with this invention, "slush ice region" is understood to mean the second region which defines the ice ball and having tissue temperatures in the range of minus $21°$ C. to about $0°$ C.

In accordance with this invention, "supra-zero hypothermia region" is understood to mean the area of the tumor tissue that has a transient and focal hypothermia about a cryoprobe defined as having a temperature in the range of about $0°$ C. to about $+37°$ C.

In accordance with this invention, the term "sclerosant" is understood to mean any agents or chemical irritants that can be used in sclerosing veins, particularly sclerosant which act by protein denaturation, or a substance which causes tissue irritation and/or thrombosis with subsequent local inflammation and tissue necrosis. Sclerosing agents can be powders, solutions, detergents, acids or bases. Although not wanting to be limited to the following chemicals, the most frequently used sclerosing agents include: absolute ethanol, hypertonic saline, hypertonic glucose, acetic acid, Polidocanol, bleomycin, Picibanil, 3% Sodium tetradecylsulfate (STS), and sclerosant foam.

In accordance with this invention, "cytotoxic drugs" means any agent or substance that kills cells, including, but not limited to, drugs with antiangiogenic properties at low dose or drugs which can be used in metronomic chemotherapy.

In accordance with this invention, the term "metronomic chemotherapy" includes low dosage and long duration chemotherapy drugs designed to minimize toxicity and target endothelium or tumor stroma as opposed to targeting the tumor. Such drugs act as DNA damaging agents, microtubule inhibitors, or to kill rapidly dividing cells.

In accordance with this invention, the term "subjecting" is defined to mean delivery of a cancerous disease inhibiting therapeutic agent in any manner known to one of skill in the art, such as, but not limited to, injection methods using a needle. In addition, the term may also be used to define delivery of the cancerous disease inhibiting therapeutic agent proceeding, subsequent to, or concurrently with any disclosed treatment regime, including but not limited to delivery of the cancerous disease inhibiting therapeutic agent proceeding, subsequent to, or concurrently with freezing/warming of a treatment region.

In accordance with the invention, the term "hypothermic treatment" is understood to mean any cold exposure treatment, including, but not limited, to cryogenic freezing or cryotherapy resulting in tissue temperatures of less than minus $21°$ C. and/or cold exposure resulting in tissue temperatures in the range of minus $21°$ C. to $+37°$ C., effective for reduction of microvasculature blood flow and sensitization to chemotherapy by cellular or molecular events associated with thermal-stress, such as, but not limited to, thermal (i.e. heat or cold) shock proteins In accordance with the invention the term "tumor" is understood to mean any tissue lesion of a human or animal body organ or structure, benign or malignant in nature that is targeted for a curative or palliative treatment. The administration of therapy can use any known means, teciniques, or approaches that is clinically recognized and approved.

Accordingly, it is a primary objective of the instant invention to teach a process for increasing the efficacy of cancerous disease inhibiting agents delivered to a treatment region of a tissue structure by exposure to cancerous disease inhibiting hypothermic treatment.

It is another object of this invention to teach a unique therapeutic, minimally invasive process to treat tumors which provides a maximized effect on the tumor, protects normal cells, and activates local pro-inflammatory cells.

It is yet another object of this invention to teach a unique therapeutic, minimally invasive process to treat tumors which provides an increase in homogenous tumor cell kill.

It is yet another object of this invention to teach a unique therapeutic, minimally invasive process to treat tumors which provides an increase in tumor cell kill in zones where cells escape thermal destruction.

It is yet another object of this invention to teach a unique therapeutic, minimally invasive process to treat tumors which provides an increase efficacy of cancerous disease inhibiting therapeutic agent delivered to a treatment region by coordinating cryotherapy with cellular and molecular events associated with a thermal stress response.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 3A is a table illustrating the effect of cryoablation and/or microencapsulated 5-fluorouracil on prostate tumor necrosis. The kill ratio of the ice ball is the ratio of tumor necrosis measured three days postoperatively to ice ball surface. It reflects the overall destructive effect of the frozen part of the thermal lesion. Combined therapy gives a larger mean necrosis radius than cryoablation alone. This difference is significant: $P<0.004$ FIG. 3B is a table illustrating the cure rate observed with a cryochemotherapy protocol that injected interstitially volume-adjusted doses of μcaps 5-FU at the time of cryoablation, perioperatively, and during the post-operative period at day 7 and day 14. Cryoablation was purposely sparing the peripheral part of bioluminescent lung tumor (A549 luc+) where the μcaps depots were injected.

DETAILED DESCRIPTION OF THE INVENTION

In the previously filed application, U.S. patent application Ser. No. 11/097,991, an enhanced and safe use of cryosurgery combined with sustained release of a cytotoxic drug, 5-fluorouracil or paclitaxel, using microencapsulation as a drug delivery system about a cryoprobe was disclosed. Use of microencapsulation as the drug delivery system allowed enhanced drug placement at a specified site. However, any effect on a specific target required movement of the drug off the carrier before the drug was capable of acting on the cells since the carrier could not penetrate the cell membrane. Drug release off the microencapsulated carrier resulted from passive diffusion through the semi-permeable membrane of the polymeric carrier and/or from lysis of the carrier at body temperature.

Figure 1:
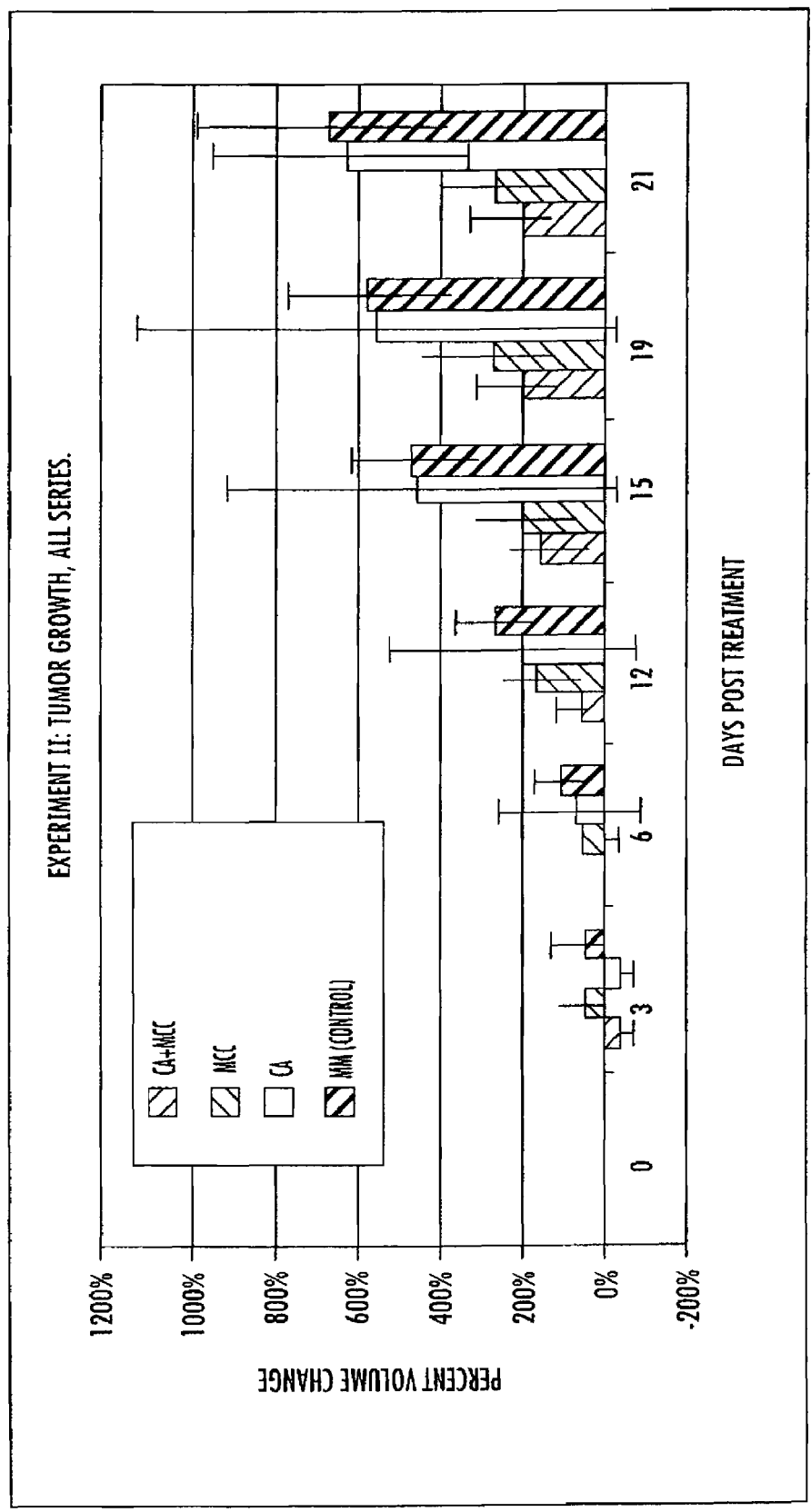
FIG. 1 illustrates enhanced inhibition of viable tumor cell growth in human prostate tumors receiving combined treatments (Cryo+5-FU μcaps) compared to increased tumor cell growth of the tumors treated with only cryosurgery. This figure demonstrates the synergistic effect of the combination of cryosurgical ablation and microencapsulated chemotherapy deposited at frozen region outer margins.
Figure 2:
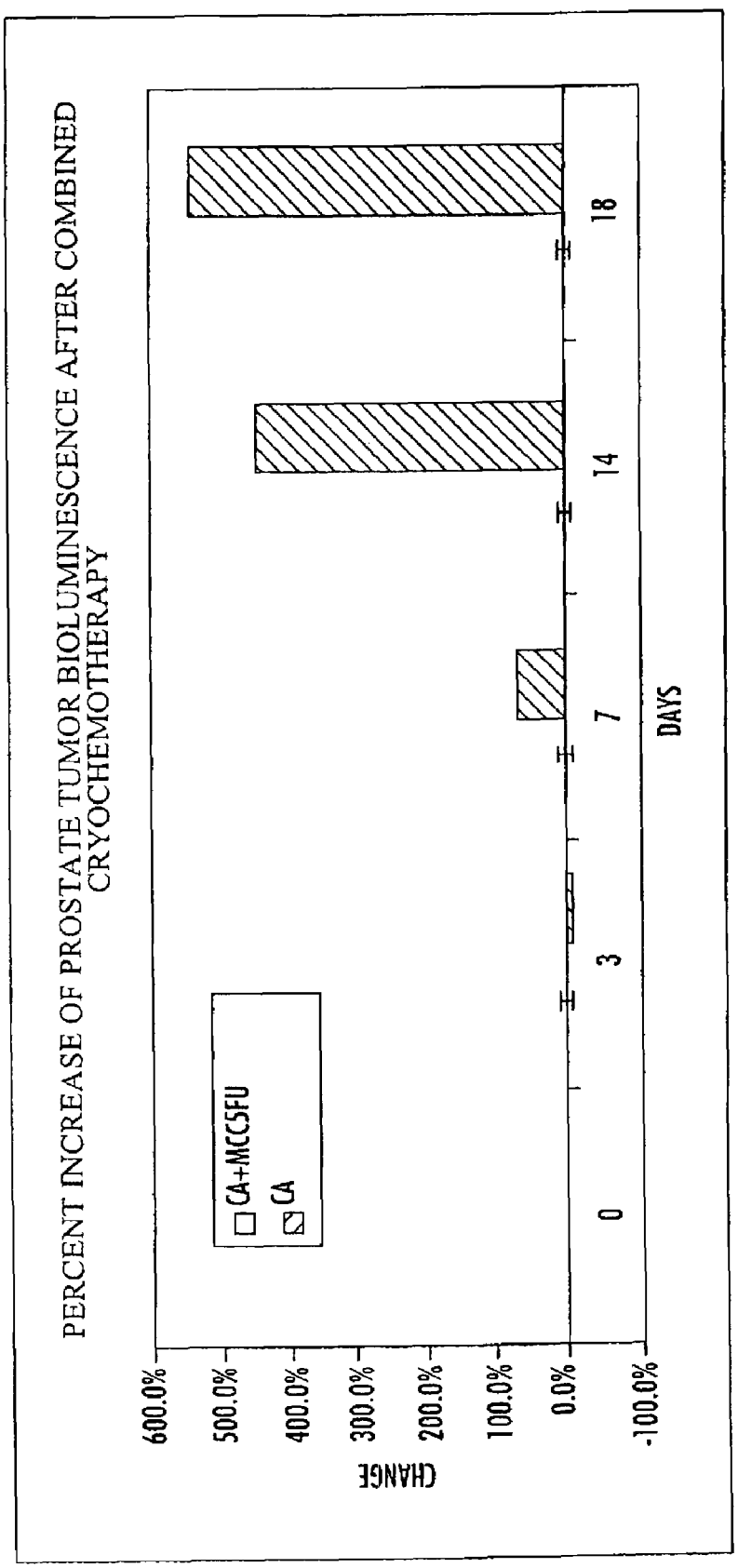
FIG. 2 illustrates the sustained release of microencapsulated drug and demonstrates the long lasting action of the sustained release of the microencapsulated drug.

This Application expands on the potential of the previously described method of combining cryosurgery with microencapsulation by disclosing a unique therapy regime to treat tumors that provides maximized effect on the tumor, protects normal cells, and activates local pro-inflammatory cells. Support for the process is based on observations of tumor growth inhibition and necrosis following cryoprobe induced moderate focal and/or whole body hypothermia and injection of microencapsulated drug at sub-lethal doses of a xenogenic lung and prostate pre-clinical tumor models. Pre-clinical tests have demonstrated that combination therapy comprised of partial freezing of a tumor before release of free drug off drug carriers has an inhibitory effect on tumor growth that is superior to each modality used individually on hormone-refractory prostate cancer and on non-small-cell lung cancer. The results of the combined modality show that cryosurgery combined with chemical agents is far more effective in inhibiting tumor growth than either individual treatment (FIGS. 1 and 2). The addition of microcapsule 5-FU also significantly increased the cryonecrotic area (see FIG. 3A), which came closer to the ice ball margin (b/t 0.5 to 1.5 mm).

Rodent tumor models were created using DU-145 human prostate carcinoma cell lines or A549 lung carcinoma cell lines which were transformed with the firefly luciferase-expressing vector. Athymic nu/nu male mice, 8-10 weeks old were subcutaneously injected in the right and left flank with $5\times10^6$ viable cells suspended in 0.1 ml solution of phosphate-buffered saline (PBS) and MATRIGEL (gelatinous protein mixture secreted from mouse sarcoma and resembles extracellular matrix environment, BD BIOSCIENCE). Solid non-necrotic tumors were treated on day 20 and 21 after implantation when they reached an average volume of about 200 mm³. All research was done with the approval of Institutional Animal Care and Use Committee of the Rumbaugh-Goodwin Institute for Cancer Research. Animals having tumors were grouped based on following treatment regimen: a) cryoablation, b) cryoablation followed immediately (during tumor thawing) by intra-tumor injection of microencapsulated 5-FU+ echogenic marker on two opposite sites of the outer unfrozen rim of the ice ball, c) Echogenic microencapsulated 5-FU deposits, "MCC/5-FU", injected on two opposite sides of a tumor periphery on day 0, 4, and 11, and d) Echogenic microcapsule markers alone (Series MM), i.e. without co-encapsulated 5-FU, Cryoablation and hypothermia treatment: Under general anesthesia a 3 mm diameter cryoprobe (Critical Care Innovations, Inc., VA, USA) is inserted vertically into tumor through a skin puncture. A 0.5 mm bead wire insulated (PFA TEFLON) type T thermocouple (Omega, CT, USA) is placed percutaneously into tumor a few mm off the probe wall. The probe tip end contains a thermocouple located at 5 mm from tip end. Both thermocouples are connected to a data-logging module (Super Logics, CP 8218) and to a laptop running a proprietary thermal monitoring and simulation software. During the cryosurgical procedure this software measures probe temperatures and uses them to predict: 1) the tumor temperature (+/−2° C.), (assuming cylindrical symmetry, by solving the equation of thermal diffusivity), and 2) ice ball formation and temperatures of tumor and adjacent tissues at various distances beyond the ice ball.

Cryoablation of experimental prostate (DU145) and lung (A549) tumors consisted of freezing a portion of the tumor from the skin surface to the deep margin and leaving a volume of peripheral tumor unfrozen but being submitted to hypothermia. The probe tip was purposely not centered in tumor so that the ice ball never overlapped the entire tumor area. Hence, the frozen zone of the tumor was clearly distinguishable from the hypothermic zone. A single freeze/thaw (F/T) cycle was used without hold time. Within 5 minutes the ice ball thawed spontaneously at room temperature. The duration of hypothermia zone in the ice ball region was estimated to be from 15 to 30 min. This time frame is clearly within the accepted duration of exposure to freezing temperatures for tumors during conventional cryoablation. The puncture was sealed with cyanoacrylate adhesive.

The relative timing of cryoablation and deposition of cancerous disease inhibiting therapeutic agents is thought to insure a synergistic effect of the combined treatment and optimal target ablation. The initial deposition of cancerous disease inhibiting therapeutic agents is made just before or after the cryogenic thermal insult. Accordingly, one skilled in the art could appreciate that depending on the tissue or type of cancer involved delivery of a cancerous disease inhibiting therapeutic agent can occur sequentially, either prior to or after, or concurrently with cryosurgery.

Figure 4A:
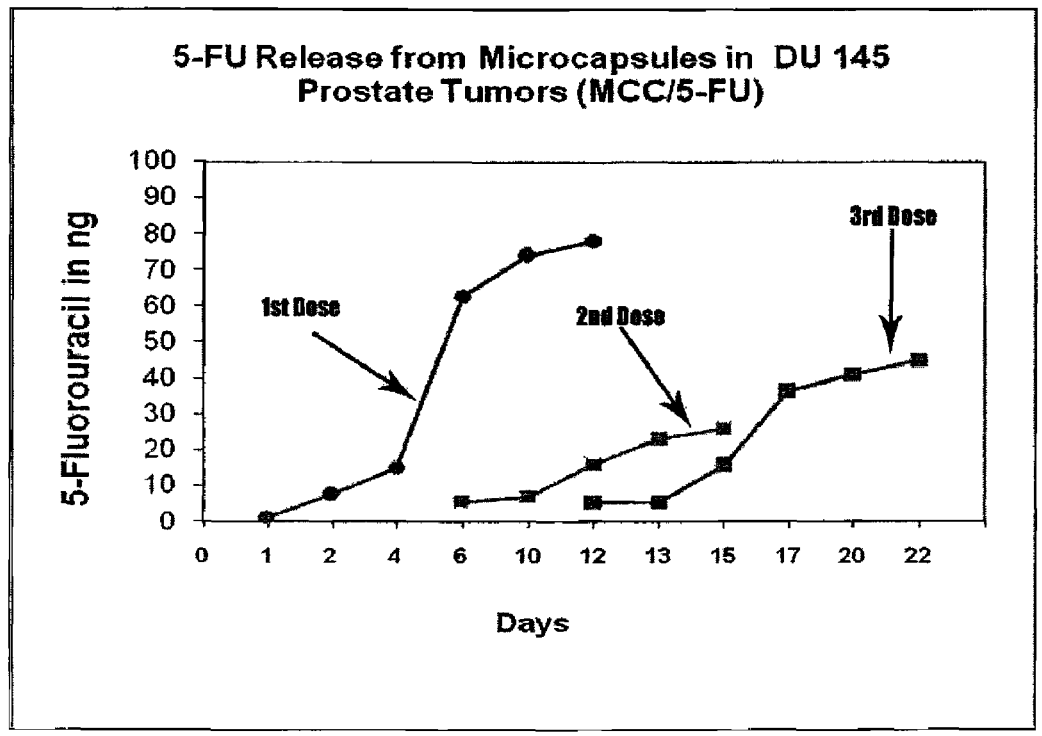
FIG. 4A is a graph representing the release of 5-FU from the microcapsules injected into various tumors at days 0, 4 and 11 for treatment group: microcapsule+5-FU treatments.
Figure 4B:
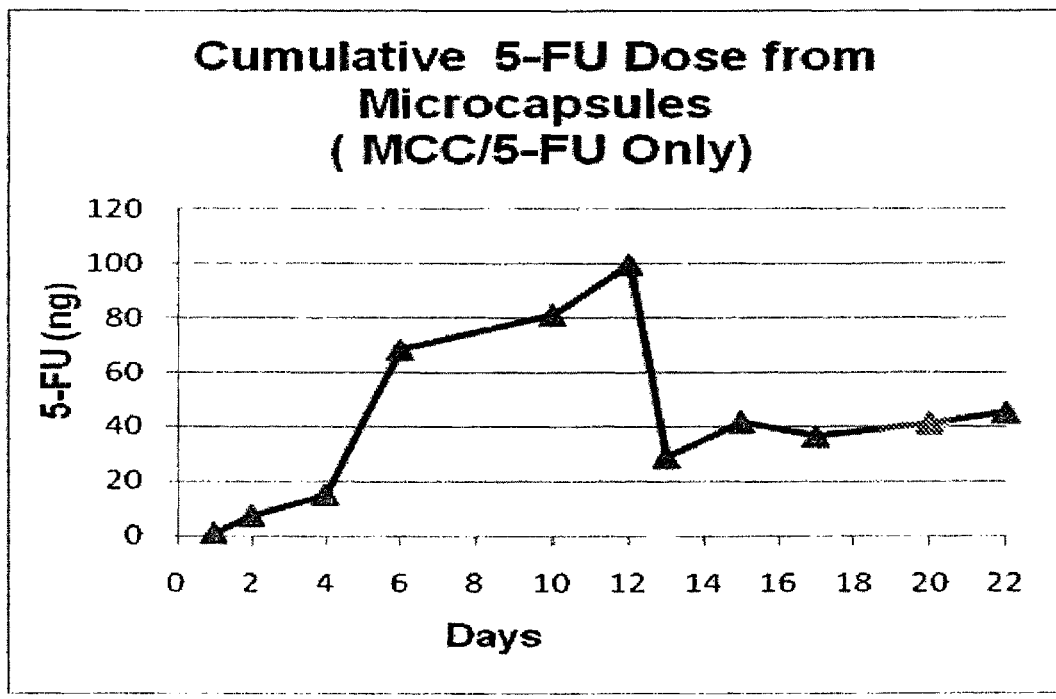
FIG. 4B is a graph representing the cumulative amount of 5-FU released from microcapsules injected at days 0 and 14 and released into tumors receiving microcapsule+5-FU.

Echogenic Microcapsules and Drug Carriers Construction: Echogenic microcapsules (MM) are tiny biocompatible and biodegradable carriers that co-encapsulate the cytotoxic drug 5-FU (Sigma), 2% w/v and 20% w/v of a dense radio and echogenic contrast oil, ETHIODIOL (Savage Labs). The average diameter of the microcapsules ranged from 9.35 to 17.83 microns (μ). The microcapsules (μcaps) were suspended in PBS and diluted to a concentration of about 65,200 μcaps per microliter (μl) (1.3×10⁶ microcapsules suspended in 20 microliters of PBS). The amount of 5-FU received by each tumor in the combined treatment group (CA+MCC/5-FU) was 96 nanogram (ng) in two doses of 20 μl of suspended microcapsules administered on Day 0 and another 45 ng on Day 14 for a total dose of 141 ng or 0.81 ng/mm3 of tumor (spared by the CA). The amount of 5-FU received by each tumor in the microcapsule only group (MCC/5-FU), from two doses of 20 μl of suspended microcapsules administered on Day 0, Day 4 and Day 11 was 149 ng or 0.81 ng/mm³ of tumor (treated). The microcapsule carriers release their 5-FU content by both diffusion and progressive lysis at body temperature. Analysis of the control microcapsules confirmed that 17% of the total drug load had been released due to capsule degradation by Day 4 after injection, and approximately 25% was released due to lysis by Day 7, and 92-95% released by Day 10. FIG. 4B shows the cumulative release of 5-FU from lysis of the microcapsules following injections on Day 0, 4, and 11. Blue, hydrophobic microspheres were mixed with the 5-FU microcapsules to aid the histological examination of the tumor tissues and facilitate re-location of the 5-FU microcapsule injection sites.

Experiments using these microcapsules indicate that 5-FU is released from the microcapsule carriers and diffuse as a free drug to the target cells. FIG. 4A is a graph representing the cumulative release of 5FU from the microcapsules injected at injected into various tumors at various times for those tumors receiving microcapsule+5-FU treatments. FIG. 4B is a graph representing the cumulative amount of 5-FU released from microcapsules released into the tumors receiving microcapsule+5-FU treatments. It is also important to note that upon injection of the microencapsulated drugs, a certain amount of the microcapsules were destroyed, releasing their contents as free drug.

Figure 5A:
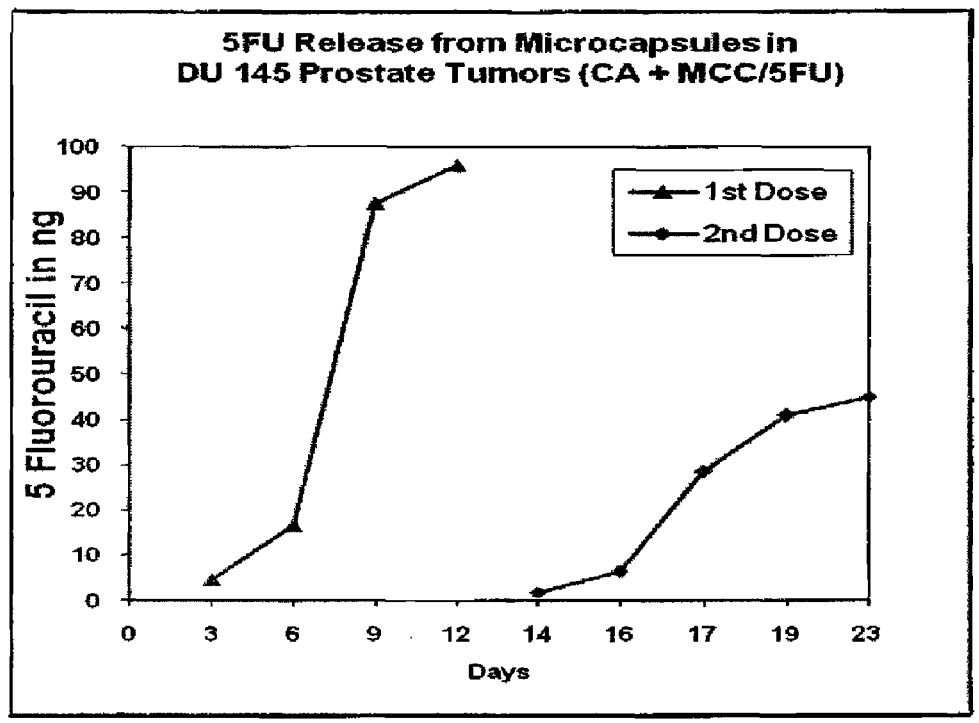
FIG. 5A is a graph representing the release of 5-FU from the microcapsules injected into various tumors at various times for those tumors which received cryoablation and microcapsule+5-FU treatments.
Figure 5B:
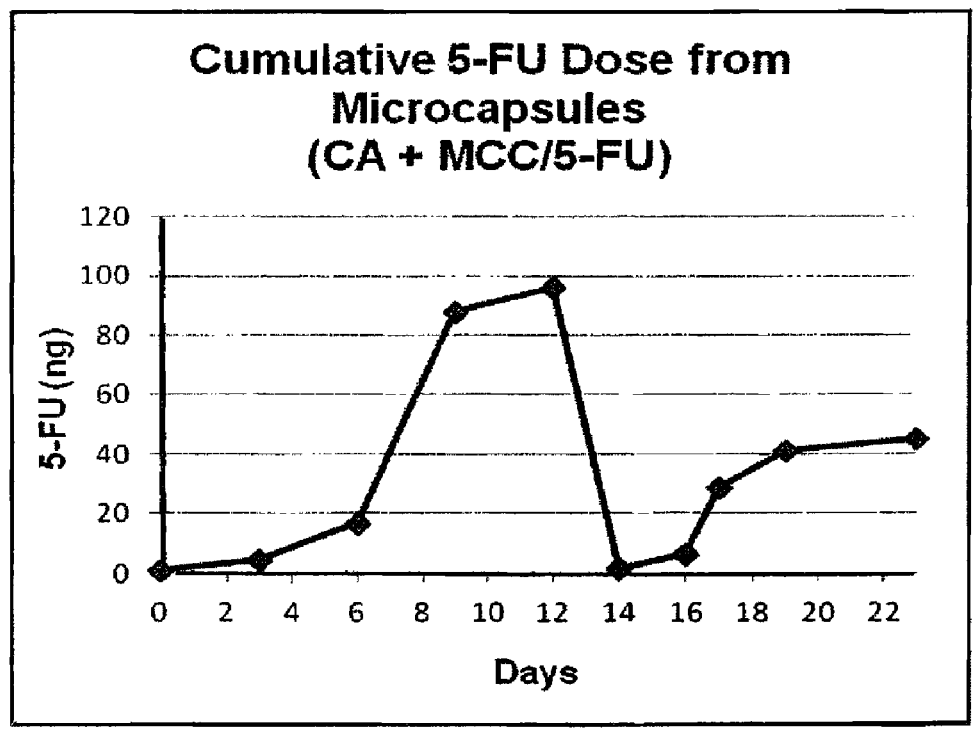
FIG. 5B is a graph representing the cumulative amount of 5-FU released from microcapsules released into tumors receiving cryoablation and microcapsule+5-FU treatments.

FIG. 5A is a graph representing the cumulative release of 5-FU from the microcapsules injected at injected into various tumors at various times for those tumors which received cryoablation and microcapsule+5-FU treatments. FIG. 5B is a graph representing the cumulative amount of 5-FU released from microcapsules released into the tumors receiving cryoablation and microcapsule+5-FU treatments. Taken together, the FIGS. 4A, 4B, 5A and 5B illustrate the time release effect and indicate the concentrations of the 5-FU for the treatment groups throughout the 22 day treatment.

Figure 6:
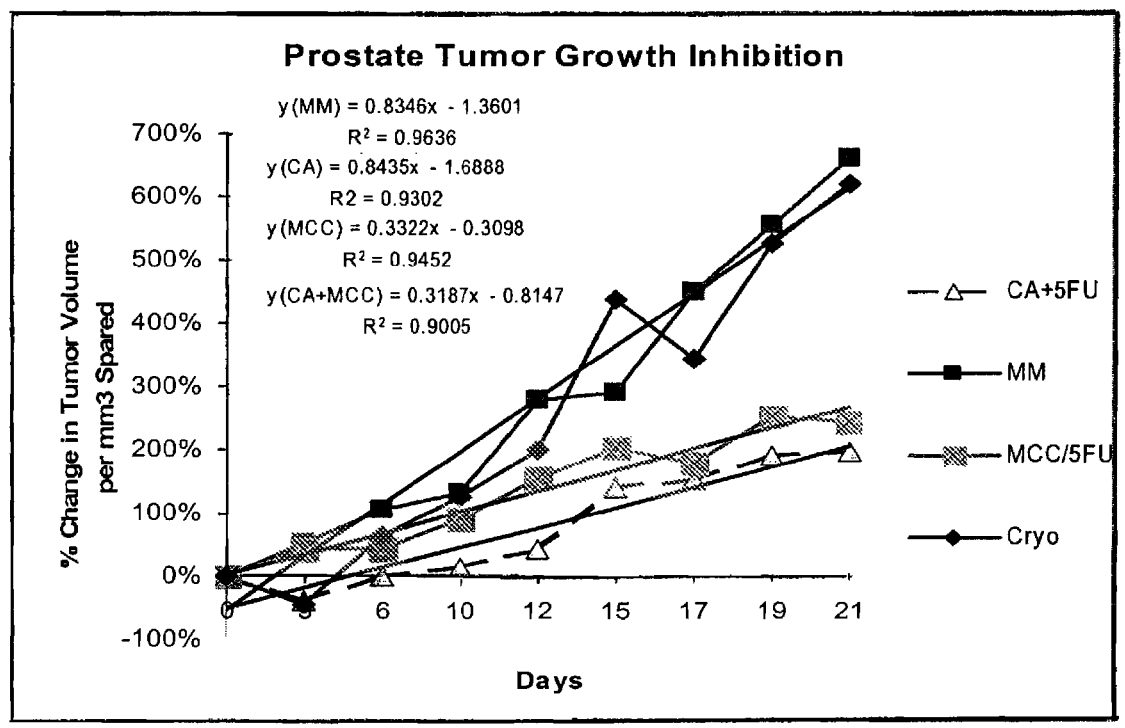
FIG. 6 illustrates the relative changes in tumor volume (normalized to $mm^3$ of spared tumor volume) and growth inhibition resulting from partial CA and 5-FU microcapsule treatments for the 21 day study. Note that the linear regression slopes for the control (MM) and the CA treated tumors are parallel and quite different from the slopes of the groups treated with microcapsules (MCC/5-FU) and the combined treatment of CA+MCC/-5FU.

As seen in FIG. 6, the effects of MCC/5-FU microcapsule deposits alone lead to an initial and sustained growth inhibition, along with a well delineated area of necrosis, located at the site(s) of deposition, and appearing within 2 to 4 days. However, overall tumor growth inhibition is much greater with the combined therapy (CA+MCC/5-FU) compared to either cryoablation alone (CA) or to the inhibition resulting from the 3 doses of microencapsulated 5-FU.

Injection of free drugs in combination with cryosurgery is not new to the art as additive or synergistic effects have been demonstrated in experimental models or human tumors. Injection of free drugs after cryosurgery has been mostly associated with systemic injection either before or after cryotreatments. Although currently being used as a treatment option, systemic injection of free drugs is unpredictable. Scientific studies reveal that there is no defined specific and optimal timing and sequence to favor trapping of an anticancer drug into a targeted lesion. Moreover, there is no assurance that the drugs injected systemically will be delivered in a sufficient concentration at the thermally challenged site. Systemic injection further has the disadvantage of possible delivery of high concentrations of drugs to healthy tissues than to the cryotreated tissues.

For injection of a cancerous disease inhibiting therapeutic agent in combination with a hypothermic treatment, such as cryosurgery, to be successful, the cancerous disease inhibiting therapeutic agent must be injected within a cryosurgically challenged target, i.e. tumor, at an effective concentration and remain at the site for prolonged period of time Moreover, a successful cancerous disease inhibiting therapeutic agent delivery system must insure that the hypothermic treatment and placement of the cancerous disease inhibiting therapeutic agent elicits vasospasms at around 15° C., vascular stasis and thrombosis at around 8° C., and drug retention. A system of injecting cancerous disease inhibiting therapeutic agents in combination with hypothermic treatment must also take advantage of enhancement of mechanisms of tumor sensitization and cell kill, such as the molecular events associated with thermal shock proteins involved in tissues subjected to hypothermic treatments. Such a system may also enhance drug diffusion toward the critical target for tumor survival, such as the microvascular bed. In addition, the cancerous disease inhibiting therapeutic agent must be delivered within specific regions of a thermally stressed tumor.

The results of our cryochemotherapy experiments on human prostate (DU-145) tumors and non-small cell lung carcinoma (A-549) tumors, using only partial freezing and very small doses of 5-FU released over 12 days from microcapsules deposited into the moderate hypothermal region of the spared tumor volume led to the development of a novel treatment process designed for more effective cryochemotherapy regimens, including combining hypothermal treatment techniques with spatial and temporal delivery of cancerous disease inhibiting agents within a treatment region. The instant inventors determined that injection of such agents in various treatment regions in coordination with the molecular or cellular events associated with thermal-related stress response increased the efficacy of cancerous disease inhibiting agents.

The cellular mechanisms as described herein are illustrative of the overall mechanisms of action of the combined cryochemotherapy treatment methods of the invention. Other molecular events, however, including other proteins and genetic changes associated with thermal stress and/or chemotherapy not specifically illustrated are within the scope of the invention. Exposure to both hyperthermia (heat shock) and hypothermia (cold shock) conditions produce many similar cellular responses, however, there are significant differences in the stress response proteins produced, the timing, and resulting cascade of molecular signals that follow. The net effect is a result in the shift of balance among competing intracellular signals, such as anti-apoptotic mediators (bcl-2) vs. pro-apoptotic mediators (caspases, Bax). Hyperthermia is well known for increasing the sensitivity of tumors to radiation and chemotherapy. However, the effects of freezing and cold exposure often produce contradictory cellular signals and thus different tumors have shown increased resistance to chemotherapy, while others appear to be sensitized by cryosurgery.

Combining thermal stress or shock, and chemotherapy involves orchestrating several cellular mechanisms to increase the efficacy in killing of the cancer cells. For effective cryochemotherapy, the resultant changes in cellular physiology caused by the cold exposure depend on the degree and duration of hypothermia, combined with specific timing and local molecular action of the cytotoxic chemotherapy drug. Since cryosurgery produces 2 frozen regions and one region of supra-zero hypothermia one must consider the immediate effects of the cellular stress produced during the cold exposure and then a large number of molecular changes that occur after re-warming in each region. A number of unique cold stress response proteins are produced as a result of cold exposure (+5 to +33° C.) as well as some of the typical heat shock proteins. Certain hypothermal effects are different in normal cells than in tumor cells, including some that protect normal cells from apoptosis and some that increase anti-apoptotic mediators in tumor cells. Also local inflammatory cells in peripheral regions exposed to moderate cold stress (+25 to 33° C.) can be triggered to secrete cytokines that affect cell growth and apoptotic mechanisms differently in both normal and tumor cells. Thus, by understanding the balance and timing of cellular cold stress responses, then selecting specific tissue and cellular changes that can be matched with complimentary molecular actions of the chemotherapy agent, it is possible to design novel cryochemo therapies that promote synergism of the cold stress response and the cytotoxic effects of certain anti-tumor drugs, as well as help protect the adjacent normal cells.

In general, more than 50 heat shock response genes (HSPs) have been characterized (Jäättelä, M, Escaping cell death: survival proteins in cancer. *Exp Cell Res.* 248(1):30-43, 1999). Severe heat shock leads to activation of apoptosis. Also, heat shock after exposure to pro-inflammatory stimuli can trigger apoptosis via activation of NFκB (DeMeester, S L, et al. The heat shock paradox: does NF-κB determine cell fate? *FASEB J* 15: 270-274, 2001). However, moderate heat stress (+40 to +42° C.) causes expression of certain HSPs that normally protect cells from progression through the cell cycle and by inhibiting cytokine induced NFκB translocation to the nucleus thus inhibiting apoptosis (see Curry, H A, et al. Heat shock inhibits radiation-induced activation of NF-kB via inhibition of I-B kinase. *J Biol Chem* 274: 23061-23067, 1999 and Yoo, C G, et al. Anti-inflammatory effect of heat shock protein induction is related to stabilization of I-B through preventing I-B activation in respiratory epithelial cells. *J Immunol* 164: 5416-5423, 2000). Heat shock causes arrest of the cell cycle (thereby protecting against apoptosis) by the expression of p53 and p21. Heat shock also increases expression of HSP70 which in turn decreases NFκB and thus inhibits apoptosis and iNOS in hepatocytes (Feinstein D L, et al Heat shock protein 70 suppresses astroglial-inducible nitric-oxide synthase expression by decreasing NF-kB activation. *J Biol Chem* 271: 17724-17732, 1996) and human pancreatic islets (Scarim, A L, et al. Heat shock inhibits cytokine-induced nitric oxide synthase expression by rat and human islets. *Endocrinology* 139: 5050-5057, 1998).

During the recovery period following heat shock (+4° C.) the stress response is known to cause an increase in synthesis and activation of p53 causing increased expression of p21 in human colorectal cancer (Ohnishi, T, et al p53-dependent induction of WAF1 by heat treatment in human glioblastoma cells. *J Biol Chem* 271: 14510-14513, 1996). Normally, an increase in p53 and p21 results in a transient cell cycle arrest (Nitta, M, et al. Heat shock induces transient p53-dependent cell cycle arrest at G1/S. *Oncogene* 15: 561-568, 1997), thereby, protecting cells from apoptosis, however, most tumor cells lack the p53 response elements therefore those cells are not protected from apoptosis. Heat shock in A549 Non-small cell lung carcinoma cells causes a decrease in TNFα and IL-8 (Yoo, C G, et al. Anti-inflammatory effect of heat shock protein induction is related to stabilization of I-B through preventing I-B. activation in respiratory epithelial cells. *J Immunol* 164: 5416-5423, 2000) and RANTES (Ayad, O, et al The heat shock response inhibits RANTES gene expression in cultured human lung epithelium. *J Immunol* 161: 2594-2599, 1998) resulting in IκBα sequestration of NFκB, thus inhibiting apoptosis.

Conventional cryosurgery methods produce three regions of low temperature and hypothermia: 1) completely frozensolid phase (hard ice), 2) partially frozen-low temperaturesolid+liquid phase (slush ice), and 3) unfrozen-liquid phasemoderate (transient temperatures below 33° C.). To understand the cellular responses to hypothermia that are important to the improved cyrochemotherapies, it is important to understand the differential effects in normal cells, cancer cells, and local inflammatory cells. In addition, it is also important to understand there are specific stress responses which occur during the cold exposure as well as during/after re-warming to normal body temperatures.

Figure 7:
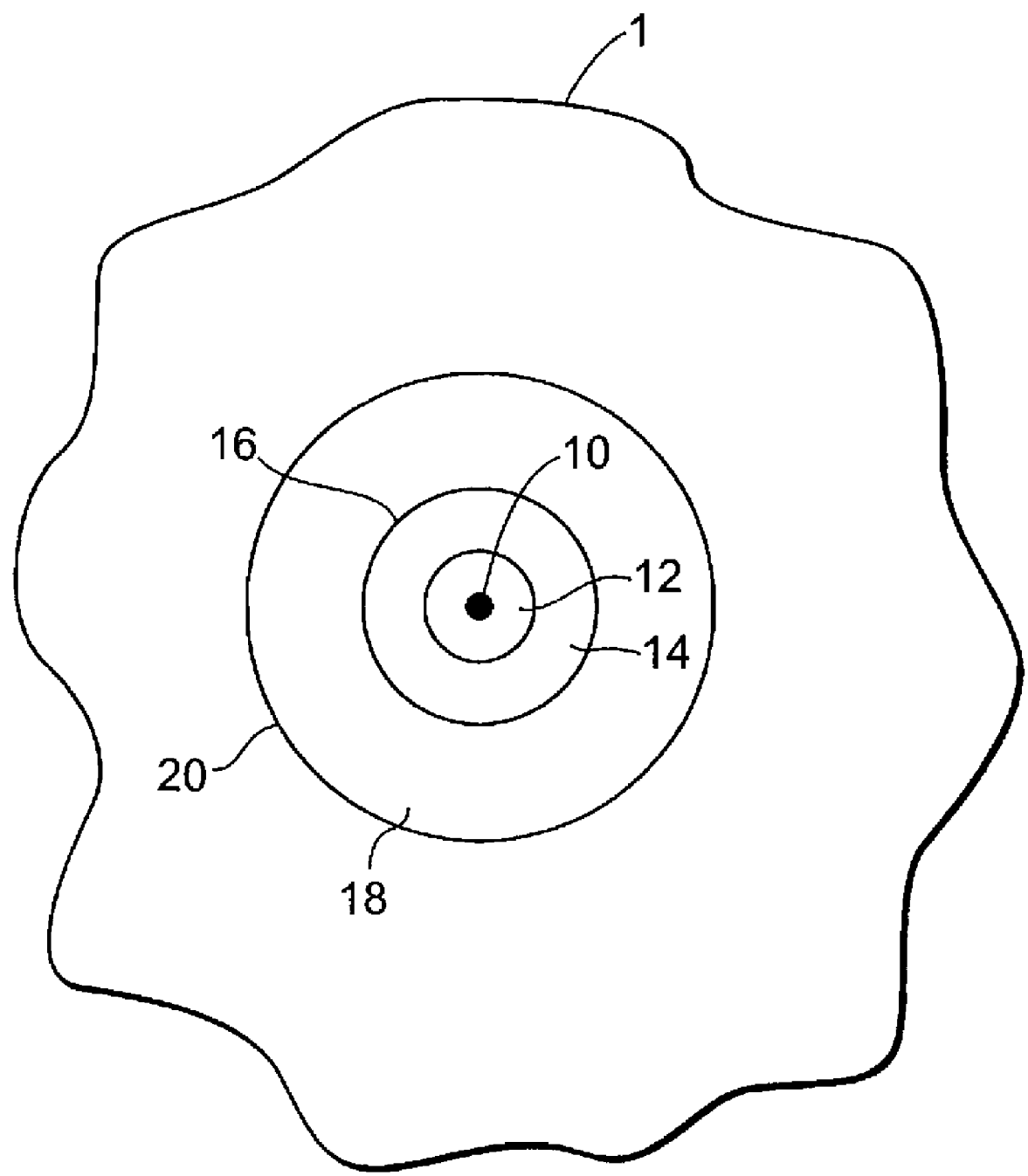
FIG. 7 is a transversal section of an ice ball during freezing, illustrating the resulting thermal regions, hard ice, slush ice and supra-zero hypothermia.

As illustrated in FIG. 7, freezing of tumor tissue 1 as a result of a cryoprobe 10 forms an ice ball (areas defined by 12 and 14) around the cryoprobe tip. The important consequences of freezing occur at both the tissue physiology level and at the molecular level and depend on several factors, including the freezing cooling speed, the nature and activity of the target cells, the time spent at freeze-cool temperatures, and warming conditions.

Within the ice ball formation, two thermal regions are produced, the "hard ice" region 12 and a "slush ice" region 14. Hard ice region 12 is defined by an area in which the temperature of the tissue is measured at any temperature less than minus 21° C. Physiological effects include extracellular and intracellular ice formation below eutectic freezing (i.e. minus 21° C.), expansion of water ice crystals to approximately 9% causing cell rupture and lysis, increase in interstitial pressure, relative local dehydration, and interruption of blood flow. Freezing to below −21 degrees Celsius further results in triggering caspases-3 and 9, degradation of PARP and other apoptosis mediators in the peripheral regions of the ice ball. These molecular events result in severely damaged cells proceeding through the cell cycle to programmed cell death.

Slush ice region 14 is defined by tissue having a temperature in the range of minus 21° C. to 0° C. Temperatures in the range of −20° C. to −2° C. result in physiological tissue changes resulting in increase in solute concentration allowing ionic motion, increase in viscosity, increase in vasoconstriction, and increase in vascular stasis, and apoptosis. No gross necrosis was observed. During cold exposure, p53 and p21 are known to increase, leading to transient cell cycle arrest and unique Cold Shock Proteins, such as CIRP- (RNA binding), RBM3, (IRES-increased efficiency of translation), NF-1 var., (alternative splicing-mRNA), KIAA0058 increase. Periods of warming following cryogenic exposure are known to increase certain cold shock proteins (Fujita, J. Cold shock response in mammalian cells. *J. Mol. Microbiol. Biotechnol.* 1: 243-255, 1999), such as HSP70, HSP90, HSP105 which lead to activation of HSF-1 binding, increase in HSP110 (osmotic stress protein e.g. AGP-1), and decrease in E-selectin (cell adhesion mediator). Additionally, increases in IL-8 during periods of warming result in phosphorylation of p38 (Gon, Y, et al. Cooling and rewarming-induced IL-8 expression in human bronchial epithelial cells through p38 MAP kinase-dependent pathway. *Biochem Biophys Res Commun* 249: 156-160, 1998).

The periphery of the slush ice region 14 defines the ice ball margin 16. Beyond ice ball margin 16 is the supra-zero hypothermia region 18. This region is defined by tissue temperatures in the range of 0° C. to +37° C. At the periphery of this region is the thermal change margin, 20. Moderate cold stress at 5° C. to 33° C. results in increased vaso-constriction (max. at +15° C.) and hemostasis (reduced blood flow), but no necrosis. Important molecular events associated with the thermal stress in this region include: release of cold shock proteins (CIRP, RBM3, KIAA0058) leading to inhibition of transcription and translation in hepatocytes (Nishiyama, H, et al. A glycine-rich RNA-binding protein mediating cold-inducible suppression of mammalian cell growth. *J Cell Biol* 137: 899-908, 1997) and enhanced translation of bone marrow stromal cells; increases in p53 and p21 leading to transient cell cycle arrest in fibroblasts (Matijasevic, Z, et al. Hypothermia causes a reversible, p53-mediated cell cycle arrest in cultured fibroblasts. *Oncol Res* 10: 605-610, 1998); increase in HSP70 and HSP90 resulting in decrease in NFκB mediated apoptosis in fibroblasts human keratinocytes (Kaneko, Y, et al A novel hsp110-related gene, apg-1, that is abundantly expressed in the testis responds to a low temperature heat shock rather than the traditional elevated temperatures. *J Biol Chem* 272: 2640-2645, 1997 and Holland, D B, et al. Cold shock induces the synthesis of stress proteins in human keratinocytes. *J Invest Dermatol* 101: 196-199, 1993); and increases in HSP105, HSP110 (AGP-1) results in increased in fibroblasts and TAMA26 Sertoli cells (Kaneko, Y, et al A novel hsp110-related gene, apg-1, that is abundantly expressed in the testis responds to a low temperature heat shock rather than the traditional elevated temperatures. *J Biol Chem* 272: 2640-2645, 1997).

The cellular or molecular events associated with thermal stress responses in cancer cells are different than normal cell responses. The cold stress response in cancer cells includes, increases in p53 and p21 in glioblastoma (Matijasevic, Z, et al. Hypothermia causes a reversible, p53-mediated cell cycle arrest in cultured fibroblasts. *Oncol Res* 10: 605-610, 1998 and Ohnishi, T, et al. p53Dependent induction of WAF1 by cold shock in human glioblastoma cells. *Oncogene* 16: 1507-1511, 1998) and CIRP and RBM3 in renal cell carcinoma (Nishiyama, H, et al. Decreased expression of cold-inducible RNA-binding protein (CIRP) in male germ cells at elevated temperature. *Am J Pathol* 152: 289-296, 1998 and Nishiyama, H, et al. A glycine-rich RNA-binding protein mediating cold-inducible suppression of mammalian cell growth. *J Cell Biol* 137: 899-908, 1997) and bladder carcinoma (T24) (Nishiyama, H, et al A glycine-rich RNA-binding protein mediating cold-inducible suppression of mammalian cell growth. *J Cell Biol* 137: 899-908, 1997), increase in NF-1 variant in human osteoblastoma U208 (Ars, E, et al. Cold shock induces the insertion of a cryptic exon in the neurofibromatosis type 1 (NF1) mRNA. *Nucleic Acids Res* 28: 1307-1312, 2000), induction of Caspase-9 and PARP degradation in colon cancer (Hanai, A, et al. Induction of apoptosis in human colon carcinoma cells HT29 by sublethal cryo-injury: mediation by cytochrome c release. *Int J Cancer.* 93(4):526-33, 2001), and caspase-3 cleavage mediated apoptosis in A-549 lung carcinoma (Forest, V, et al. In vivo cryochemotherapy of a human lung cancer model. *Cryobiology.* 51(1):92-101, 2005). Moreover, stress response changes associated with re-warming following cold exposure include increases in Apoptosis Specific Protein-1 in lymphoma (MUTU-BL) (Grand, R J, et al. A novel protein expressed in mammalian cells undergoing apoptosis. *Exp Cell Res* 218: 439-451, 1995), p53 and p21 in glioblastoma (A-172) (Matijasevic, Z, et al. Hypothermia causes a reversible, p53-mediated cell cycle arrest in cultured fibroblasts. *Oncol Res* 10: 605-610, 1998), HSP70 in squamous cell carcinoma (Kaneko, Y, et al. A novel hsp110-related gene, apg-1, that is abundantly expressed in the testis responds to a low temperature heat shock rather than the traditional elevated temperatures. *J Biol Chem* 272: 2640-2645, 1997), and bcl-2 in prostate cancer cells (PC3) (Clarke, D M, et al. Addition of anticancer agents enhances freezing-induced prostate cancer cell death: implications of mitochondrial involvement. *Cryobiology.* 49(1):45-61, 2004) causing inhibition of apoptosis. In addition to the effects on normal and cancer cells, thermal stress also has an effect on the inflammatory response. Extreme cold or heat can cause necrosis and significant apoptosis in tissues that releases pro-inflammatory stimuli, thus mobilizing immune cells to invade the tissues. Cold shock, in regions where no necrosis or apoptosis has yet occurred, has unique effects on predominantly monocytic cells that influence their normal immune functions, antigen recognition, and cytokine secretions. These cold stress effects, in turn, have subsequent consequences on the cellular physiology in local normal tissues and in sometimes in tumors that previously escaped attack by regional immune cells.

The major effects of deep and moderate hypothermia on immune cells in tissues peripheral to tumors treated with cryosurgery are important in selecting chemotherapeutic drugs that will be synergistic with cryosurgery. It is also important for designing chemotherapy and cytokine cocktails to increase the cytotoxic effects on the tumor cells, while protecting the recovery of adjacent normal cells. Mild to moderate cold stress results in a 60-70% decrease in colliqin1 and 2; HSP47, HSP70, HSP105, HSP 110 (APG-1; osmotic shock protein), TUSC-4 (tumor suppressor protein), bcl-11a (immune mediator), and RBM 10 (RNA binding protein). HSP70 is known to be necessary for the survival of tumor cells so a decrease in HSP70 stimulates tumor cell apoptosis. Lower levels of HSP70 also enhances NFkB gene dependent expression which increases apoptosis in nearby cells upon release from inflammatory cells; Decrease in HSP47 is in contrast to increase in normal non-immune cells.

Additionally, moderate cold stress produces 2 to 7-fold increase in: expression of cytokines, such as CD14 and TNFa (that promote apoptosis); growth and proliferation factors, such as ICAT-1, Growth Arresting Specific-7 (GAS-7); Insulin-like Growth Factor-1 (Somatomedin C) leading to cell growth and proliferation; Cold Stress Protein increases, such as Cyclophilin A, CIRP (increased RNA stability); protein synthesis, such as B3GALT4 (post translational processing), MAFF (transcription factor), and others; and NF-1 variant (signal transduction for mRNA splicing) in human peripheral blood lymphocytes {and human fibroblasts (Ars, E, et al. Cold shock induces the insertion of a cryptic exon in the neurofibromatosis type 1 (NF1) mRNA. *Nucleic Acids Res* 28: 1307-1312, 2000).

Although not wanting to be limited to a particular mechanism, several illustrative events are believed to play an important role in the increased efficacy of cancerous disease inhibiting therapeutic agents associated with the process. The physiological mechanisms associated with the cold exposure include, vaso-constriction, (Vasospasm max at +15° C.), blood homeostasis, slower drug washout, longer absorption time at cell level, and increase in the vascular endothelial cell permeability of tumor vessels and subsequent increased perfusion of the chemotherapy agents. Cell Freezing (−21° C. to 0° C.) provides ice formation and leads to ice cell lysis and triggering apoptosis in the kill zone. Cold stress response at 1° C. to 28° C. produces two groups of stress proteins that effect apoptosis mechanisms which are peripheral to kill zone but active in slush ice and supra-zero hypothermia regions.

A first set of cold stress proteins are released only during cold stress and are thought to work in conjunction with the mechanisms of action of the cancerous disease inhibiting therapeutic agents to increase effectiveness of the agents. In addition, pro-apoptosis mechanisms are thought to be triggered that work later in combination with the cytotoxic drug action as it is released over a sustained period of time. Cold stress proteins increased during exposure to hypothermia (+15 to +33° C.) in normal cells include: NF-1 variant (fibroblasts) which increase signal transduction by alternative splicing of pre-mRNA (Ars, E, et al. Cold shock induces the insertion of a cryptic exon in the neurofibromatosis type 1 (NF1) mRNA. *Nucleic Acids Res* 28: 1307-1312, 2000); CIRP (Cold Inducible RNA Binding Protein) increases RNA binding, causes increased transcription which suppresses mitosis and arrests cell cycle progression (hepatocytes, Chappell, S A, et al. A5 leader of Rbm3, a cold stress-induced mRNA, mediates internal initiation of translation with increased efficiency under conditions of mild hypothermia. *J Biol Chem* 276: 36917-36922, 2001); RBM3 (Internal ribosome entry site, IRESs) which is involved in enhanced efficiency of translation thru IRES, 5' leader sequence arrests cell cycle progression (Danno, S, et al. Decreased expression of mouse Rbm3, a cold-shock protein, in Sertoli cells of cryptorchid testis. *Am J Pathol* 156: 1685-1692, 2000 and Danno, S, et al Increased transcript level of RBM3, a member of the glycine-rich RNA-binding protein family, in human cells in response to cold stress. *Biochem Biophys Res Commun* 236: 804-807, 1997); and ATPase subunit 6 and 8 which results in increased efficiency of translation (normal cells) (Ohsaka, Y, et al. Mitochondrial genome-encoded ATPase subunit 6+8 mRNA increases in human hepatoblastoma cells in response to nonfatal cold stress. *Cryobiology* 40: 92-101, 2000) in comparison to inhibition of RNA degradation in tumor cells.

A second set of stress proteins which are responsible for delayed effects, are released during warming of the cryogenically frozen tissue to body temperature. While these stress proteins may have some direct effect on apoptosis, the delayed onset allows for indirect, long lasting (HSP90 and p53 increased) effects, which peak at 48 hours. The delayed effects therefore provide for a mechanism to sensitize tumor tissues to the drug slowly released from the chemo-microcapsules. Stress proteins, such as p53, p21, HSP-70, HSP90a are increased and protect normal cells in the tumor region from progression through the cell cycle, despite the fact the tumor cells get promoted into cell cycle progression and increased secretion of NFkB, leading to apoptosis. Release of these proteins depends on the temperature and duration of cold exposure.

In addition to activation of the cold stress proteins in normal and tumor cells, cold exposure activates ancillary immune cells. The apparent opposing effects of cold stress on the dormant immune cells located near the tumor illustrate selected cold stress responses that results in release of cytokines promoting apoptosis (TNFa, CD14), growth factor inhibitors (GAS-7), CIRP, RBM3, and pro-inflammatory secretions that in turn can augment the action of 5-FU and other cytotoxic agents that act by inducing apoptosis in susceptible tumor cells.

Based on these molecular mechanisms, the inventors developed a unique therapy treatment comprising the steps of exposing a treatment area to hypothermic treatment, such as cryogenically freezing a treatment region, which results in formation of one or more regions selected from a hard ice region, a slush region, and a supra-zero hypothermia within the treatment region and inducing at least one cellular or molecular event, including but not limited to tumor cell sensitization to cancerous disease inhibiting therapeutic agents, protection of normal cells, activation of pro-inflammatory responses, or combinations thereof, associated with a thermal-related stress response, and subjecting the hard ice region, slush region, supra-zero hypothermia, or combinations thereof, to the effects of the cancerous disease inhibiting therapeutic agent. The effects of the cancerous disease inhibiting therapeutic agent may range from instantaneous, to hours, days or longer, or may be the result of time release depending on the particular cancerous disease inhibiting therapeutic agent, location of delivery, or delivery method. Since it is known in the art that all tumor cells respond to cold stress via release of thermal shock proteins, it is within the embodiment of the invention that all tumors, not just prostate and lung cancer as illustrated herein may be treated by the disclosed process.

At certain times during short cold exposure, critical stress responses occur which can be coordinated with the proper timing of apoptotic chemotherapy drug action (released over 10-12 days, max. effect 4-5 days after single bolus administration). Selected apoptosis mediators are up-regulated during short duration exposure to moderate temperatures which lead to cold stress proteins that sensitize and promote apoptosis in tumor cells to chemotherapy drug induced apoptosis through expression of caspases, degradation of PARP, greater release of apoptosis mediators than cryo-induced release of anti-apoptotic mediators (bcl2, etc).

There are several advantages to selecting cold stress responses at the cellular level which enhance the apoptotic effects of certain drugs, such as 5-FU and other similar cytotoxic chemotherapeutics. Cold shock proteins promote pro-apoptotic mediators in tumor cells, overwhelming the anti-apoptotic mediators within the tumor cells, thereby sensitizing those tumor cells to the chemo-drug mechanisms that promote programmed cell death (apoptosis). Second, selected cold shock proteins that protect normal cells in moderate hypothermia regions do not protect tumor cells. Finally, some cold shock proteins stimulate local inflammatory cells near the tumor (mild to moderate hypothermia regions) that increase secretions of cytokines which further promote apoptotic mediators, thus indirectly enhancing the pro-apoptosis effects of the chemo-drug.

Because some cold shock proteins are produced during cold exposure and others are produced during re-warming the process is based on the relative timing of the cold stress. The overall timing of the cold stress response can be designed in advance and controlled by cryo-surgery temperature monitoring techniques that allow short exposure at warmer hypothermia temperatures to produce the desired pro-apoptotic effects and thus produce increased efficacy of certain chemotherapy drugs that are released over a 10-12 day period from chemo-microcapsules.

Direct delivery of cancerous disease inhibiting therapeutic agents with cryotherapy increases efficiency of apoptotic chemo-drugs in tumor cells as a result of increases in cold shock proteins during cold, which has cumulative effects of enhancing membrane transport, inhibiting mRNA degradation, and increased efficiency of translation and synthesis of pro-apoptotic mediators that, in turn, has a net effect of shifting the balance of pro-apoptotic mediators over that of the anti-apoptotic mediators, thus greatly increasing the efficacy of chemo-drugs by promoting tumor cell progression through the cell cycle and triggering programmed cell death (apoptosis).

Molecular events associated with tumor cells leading to increased apoptosis include up-regulated caspase-3, increase in caspase-9, and increased PARP degradation. CIRP and RBM3 are up-regulated which increase efficiency of RNA binding and translation (synthesis) of critical signal proteins. Notably, an increase in p53 and p21 does not protect tumor cells by transient inhibition of progression through the cell cycle and does not work in p53 deficient tumor cells. Therefore, tumor cells are not spared from chemo-induced apoptosis. Molecular events associated with protective effects during cold exposure on normal cells include, up-regulation of p53 and p21 leading to transient inhibition of cell cycle to inhibit apoptosis, decrease in E-selectin, increase in ATPase leading to inhibition of RNA degradation which in turn promotes synthesis of additional cold shock proteins, induction of CIRP within 3 hours after temperature reduction that indirectly suppresses growth and progression through cell cycle which protect normal cells from apoptosis effects of chemo-drug, and increase in RBM3 which promotes translation of mRNA mediators which promote protein synthesis at reduced temperatures (33° C.).

In another illustrative embodiment, the process comprises the steps of exposing a treatment region to hypothermic treatment which results in formation of one or more regions selected from a hard ice region, a slush ice region, and a supra-zero hypothermia region within the treatment region and induces at least one cellular or molecular event, including but not limited to tumor cell sensitization to cancerous disease inhibiting therapeutic agents, protection of normal cells, activation of pro-inflammatory responses, or combinations thereof, associated with a thermal-related stress response; and subjecting the hard ice region, slush region, supra-zero hypothermia supra-zero, or combinations thereof, to the effects of a cancerous disease inhibiting therapeutic agent in conjunction with warming of the hypothermic treated tissue.

Selected effects of certain cold stress proteins produced which enhance apoptotic effects cancerous disease inhibiting therapeutic agents on tumor cells during warming include, increased expression of Apoptotic specific protein (ASP) peripheral to the kill zone, increased expression of HSP105 and HSP110 leading to activation of HSF-1 and increased synthesis of apoptosis mediators, decrease in HSP70 leading to increased NFkB and increased apoptosis, and increase in HSP90a which leads to increased apoptosis at 48 hours. Several events which have protective effects on normal cells during re-warming include, induction of selected cold shock proteins that produce inhibition of synthesis of pro-apoptotic mediators and transient inhibition of progression through cell cycle in normal cells so programmed cell death is not triggered by the pro-apoptotic effects of the chemo-drug include, increased production of HSP70 and HSP90 leading to decreasing NFkB and inhibiting apoptosis in normal cells, increases in p53 and p21 that cause transient inhibition of progression through cell cycle thus protecting normal cells until the transient pro-apoptotic effects of the cytotoxic drugs and subsequent increase of apoptotic mediators, and increase in IL-8. Finally, selected effects of certain cold stress proteins on local immune cells which increase apoptotic effects of chemo-drug on tumor cells include, increased expression of CD14 mediated release of TNF-a (Chao, BH and Bischof, JC. Pre-treatment inflammation induced by TNF-alpha augments cryosurgery injury on human prostate cancer, *Cryobiology* 49(1):10-27, 2004), IL-1b and IL-6 from monocytes, decreased expression of HSP70 that enhances NFkB dependent expression of apoptosis mechanisms, HSP47, APG-1 (osmotic shock protein) in THP-1 monocytic, increases expression of Growth arresting specific protein 7, and ICAT-1, IGF-1, increase in HSP105, and HSP110—which leads to activation of HSF-1 and increased synthesis of apoptosis mediators, decreased HSP70 decreased in THP-1 leukemia cells leading to increased NFkB and increase in HSP90a leading to increased apoptosis at 48 hours (Wang, H, et al. Analysis of the activation status of Akt, NFkappaB, and Stat3 in human diffuse gliomas. *Lab Invest.* 84(8):941-51, 2004).

In another illustrative embodiment, several independent steps, or combinations thereof, steps are performed, including: 1) Ultrasound imaging to characterize a tumor, determining location, volume, and size and shape; 2) calculation of tumor dimensions and determination of frozen region parameters, ice ball parameters, and/or determination of supra-zero hypothermia region parameters; 3) Ultrasound guidance of and precise positioning of one or more cryoprobes and/or any instrument that reduces tissue temperature or injects, with or without a vibrating tip at a selected location into the tumor as deemed necessary by the surgical team; 4) exposure of the tumor to hypothermic treatment, including but not limited to, computer-aided and image guided cryoablation with a single freeze session per probe and no hold time at minimal temperature, to monitor ice ball growth within the edges of the tumor; 5) creation of freeze region (i.e. ice ball, including hard ice/slush ice regions) and supra-zero hypothermia region which induce at least one cellular or molecular event, including but not limited to tumor cell sensitization to cancerous disease inhibiting therapeutic agents, protection of normal cells, activation of pro-inflammatory responses, or combinations thereof, associated with a thermal-related stress response; 6) percutaneous injection of cancer disease inhibiting therapeutic agent into any area, such as margins, periphery or center, calculated to reside in the hard ice region, slush ice region, supra-zero hypothermia region, or combinations thereof. Alternatively, percutaneous injection of cancer disease inhibiting therapeutic agent into any area, such as margins, periphery or center, calculated to reside in the hard ice region, slush ice region, supra-zero hypothermia region, or combinations thereof, can be performed in conjunction with warming of said hypothermic treated tissue. Injection of the cancer disease inhibiting therapeutic agent is accomplished by use of a needle, or the like, constructed and arranged for different conformations for simultaneous cryosurgery and or hypothermia, and injection of the agents. In a particular embodiment, the cancerous disease inhibiting therapeutic agent is preferably injected within the supra-zero hypothermia region. In another alternative embodiment, injection of the cancer disease inhibiting therapeutic agents is performed prior to or concurrently with the freezing of the treatment area.

According to an additional illustrative embodiment, cancerous disease inhibiting therapeutic agents are injected into any area corresponding to the hard ice region prior to the hypothermic treatment of the tissue. In this manner, cancerous disease inhibiting therapeutic agents are free to diffuse and act upon other regions as the tissue thaws. Such a mechanism allows additional opportunity for cellular kill for those cells that may have escaped the initial cell kill resulting from cryoinjury.

In addition, cancerous disease inhibiting therapeutic agents may be supplied in an encapsulated (microencapsulated) form, alone or in combination with cancerous disease inhibiting therapeutic agents, and injected into any of the thermal regions. One of the main advantages of using encapsulated drug is a delayed effect, with drug actions starting at 24-48 hours post depositing. Proposed mechanism of action include thermal sensitization of tumor tissue resulting through p53 and cycling tumor tissue lacking p53 expression, apoptosis triggering through thermal induction of heat shock proteins (HSPs, class HSP-90), and retention of cancerous disease inhibiting therapeutic agents and preferential diffusion to regions of drainages, such as microvascular networks. In addition, any drug encapsulated must be freed from the capsule degradation. The drug must be capable of diffusing from the site of encapsulation and deposition to areas of interest. Moreover, microcapsule concentrations must be calculated for targeted tumors. Such an encapsulated form has the benefit of slow release of the encapsulated cancerous disease inhibiting therapeutic agent for several days, such as for 10-12 days.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for increasing the efficacy of cancerous disease inhibiting therapeutic agents delivered to a tumor in need thereof comprising the steps of:
    exposing a predetermined volume of said tumor to hypothermic treatment resulting in formation of one or more regions selected from a hard ice region, a slush region, and a supra-zero hypothermia region within said tumor;
    inducing at least one cellular or molecular event associated with a thermal stress response resulting in the expression of one or more cold stress proteins which promote one or more pro-apoptotic mediators in said tumor that works synergistically with a sustained release microencapsulated cancerous disease inhibiting therapeutic agent; and
    delivering said sustained-release microencapsulated cancerous disease inhibiting therapeutic agent to said tumor when said cold stress proteins are expressed, thereby sensitizing said tumor to the effects of said therapeutic agent by promoting programmed cell death;
    whereby the increased efficacy of cancerous disease inhibition of said therapeutic agent within said treatment region results from the interaction of said mediators and the available sustained released agent.

2. The process according to claim 1 wherein said therapeutic agent is further delivered during the period when one or more cold stress response proteins are expressed thereby resulting in thermal cellular stress that combines with said microencapsulated agent action to simultaneously sensitize said tumor to inhibition rendered by said agents and at the same time acts to protect normal cells by inhibiting cell cycle progression.

3. The process according to claim 1 wherein said therapeutic agent is released from said microencapsulation in a time dependent manner such that said release of said therapeutic agent is released to said slush region over a time period greater than one day.

4. The process according to claim 2 wherein said therapeutic agent is released from said microencapsulation in a time dependent manner such that said release of said therapeutic agent is released to said slush region over a time period greater than one day.

5. The process according to claim 1 wherein said cancerous disease inhibiting therapeutic agent is a mixture of at least one cytotoxic drug and at least one immune stimulant or cytokine.

6. The process according to claim 3 wherein said cancerous disease inhibiting therapeutic agent is a mixture of at least one cytotoxic drug and at least one immune stimulant or cytokine.

7. The process according to claim 4 wherein said cancerous disease inhibiting therapeutic agent is a mixture of at least one cytotoxic drug and at least one immune stimulant or cytokine.

8. The process according to claim 1 wherein said cancerous disease inhibiting therapeutic agent is 5-fluorouracil or paclitaxel.

9. The process according to claim 3 wherein said cancerous disease inhibiting therapeutic agent is 5-fluorouracil or paclitaxel.

10. The process according to claim 4 wherein said cancerous disease inhibiting therapeutic agent is 5-fluorouracil or paclitaxel.

11. A process for increasing the efficacy of cancerous disease inhibiting therapeutic agents delivered to a tumor in need thereof comprising the steps of:
    exposing a predetermined volume of said tumor to hypothermic treatment resulting in formation of one or more regions selected from a hard ice region, a slush ice region, and a supra-zero hypothermia within said tumor;
    inducing at least one cellular or molecular event associated with a thermal stress response resulting in the expression of one or more cold stress proteins or a combination of heat and cold shock proteins that together promote one or more pro-apoptotic mediators in said tumor that works synergistically with a sustained release microencapsulated cancerous disease inhibiting therapeutic agent;
    allowing said hypothermically treated tumor volume to warm; and
    delivering-said sustain-released microencapsulated cancerous disease inhibiting therapeutic agent to said tumor when said cold stress proteins are expressed, during said warming of said hypothermic treated tumor, thereby sensitizing said tumor to the effects of said therapeutic agent by promoting programmed cell death or other proliferation inhibiting mechanisms;
    whereby the increased efficacy of cancerous disease inhibition of said therapeutic agent within said treatment region results from the interaction of said mediators and available sustained released agent.

12. The process according to claim 11 wherein said therapeutic agent is further delivered during the period when one or more cold stress proteins are expressed, thereby resulting in thermal cellular stress that combines with said microencapsulated agent action to simultaneously sensitize said tumor to inhibition rendered by said agent and at the same time acts to protect normal cells by inhibiting cell cycle progression.

13. The process according to claim 11 wherein said cancerous disease inhibiting therapeutic agent is released from said microencapsulation in a time dependent manner such that said release of said therapeutic agent is released to said slush region over a time period greater than one day.

14. The process according to claim 12 wherein said cancerous disease inhibiting therapeutic agent is released from said microencapsulation in a time dependent manner such that said release of said therapeutic agent is released to said slush region over a time period greater than one day.

15. The process according to claim 11 wherein said cancerous disease inhibiting therapeutic agent is 5-fluorouracil or paclitaxel.

16. The process according to claim 13 wherein said cancerous disease inhibiting therapeutic agent is 5-fluorouracil or paclitaxel.

17. The process according to claim 14 wherein said cancerous disease inhibiting therapeutic agent is 5-fluorouracil or paclitaxel.

18. The process according to claim 11 wherein said therapeutic agent is further delivered when one or more cold stress proteins are expressed, said proteins initiating the release of mediators that stimulate a pro-inflammatory response.

19. The process according to claim 12 wherein said therapeutic agent is further delivered when one or more cold stress proteins are expressed, said proteins initiating the release of mediators that stimulate a pro-inflammatory response.

20. The process according to claim 13 wherein said therapeutic agent is further delivered when one or more cold stress proteins are expressed, said proteins initiating the release of mediators that stimulate a pro-inflammatory response.

21. A process for increasing the efficacy of cancerous disease inhibiting therapeutic agents delivered to a tumor in need thereof comprising the steps of:
    determining the size, shape, location, volume, or combinations thereof, of a tumor to be treated;
    determining the parameters of the area within said tumor to be frozen;
    exposing a predetermined volume of said tumor to hypothermic treatment, said exposure resulting in lowering of the temperature of at least a portion of said volume to a temperature of between about −21 degrees C. and about −40 degrees C. to form a hard ice region, a slush ice region, and a supra-zero hypothermia region;
    inducing at least one cellular or molecular event associated with a thermal stress response resulting in the expression of one or more cold stress proteins which promotes one or more pro-apoptotic mediators in said tumor that works synergistically with a sustained release microencapsulated cancerous disease inhibiting therapeutic agent; and
    delivering said sustained release microencapsulated cancerous disease inhibiting therapeutic agent to said tumor when said cold stress proteins are expressed, thereby sensitizing said tumor to the effects of said therapeutic agent by promoting programmed cell death;
    whereby the increased efficacy of cancerous disease inhibition results from the interaction of said mediators and available sustained released agent.

22. The process according to claim 21 wherein said therapeutic agent is further delivered during the period when one or more cold stress proteins are expressed, thereby resulting in thermal cellular stress that combines with said microencapsulated agent action to simultaneously sensitize said tumor to inhibition rendered by said agent and at the same time acts to protect normal cells by inhibiting cell cycle progression.

23. The process according to claim 21 wherein said cancerous disease inhibiting therapeutic agent is released from said microencapsulation dependant manner to correspond to one or more said cellular or molecular events associated said thermal-related stress response.

24. The process according to claim 22 wherein said cancerous disease inhibiting therapeutic agent is released from said microencapsulation in a time dependant manner to correspond to one or more said cellular or molecular events associated with said thermal-related stress response.

25. The process according to claim 21 wherein said cancerous disease inhibiting therapeutic agent includes at least one cytotoxic drug and at least one immune stimulant or cytokine.

26. The process according to claim 24 wherein said cancerous disease inhibiting therapeutic agent includes at least one cytotoxic drug and at least one immune stimulant or cytokine.

27. The process according to claim 21 wherein said cancerous disease inhibiting therapeutic agent is 5-fluorouracil or paclitaxel.

28. The process according to claim 21 wherein said cancerous disease inhibiting therapeutic agent is 5-fluorouracil or paclitaxel.

29. The process according to claim 21 wherein exposure of said tumor to said hypothermic treatment further includes at least one cryoprobe.

30. A process for delivering cancerous disease inhibiting therapeutic agents to a tumor comprising the steps of:
  determining the size, shape, location, volume, or combinations thereof of a tumor to be treated;
  determining the parameters of the area of said tumor to be frozen;
  exposing a predetermined volume of said tumor to hypothermic treatment, said exposure resulting in lowering of the temperature of at least a portion of said volume to a temperature of between about −21 degrees C. and about −40 degrees C. to form a hard ice region, a slush ice region, and a supra-zero hypothermia region;
  inducing at least one cellular or molecular event associated with a thermal stress response resulting in the expression of one or more cold stress proteins, or a combination of heat and cold shock proteins, that together promote one or more pro-apoptotic mediators in said tumor that works synergistically with a sustained release microencapsulated cancerous disease inhibiting therapeutic agent;
  allowing said hypothermically treated tumor volume to warm; and
  delivering said sustained release microencapsulated cancerous disease inhibiting agent to said tumor when said cold stress proteins are expressed during said warming of said tumor, thereby sensitizing said tumor to the effects of said therapeutic agent by promoting programmed cell death;
  whereby the increased efficacy of cancerous disease inhibition results from the interaction of said mediators and available sustained released agent.

31. The process according to claim 30 wherein said therapeutic agent is further delivered during the period when one or more cold stress proteins are expressed, thereby resulting in thermal cellular stress that combines with said microencapsulated agent action to simultaneously sensitize said tumor to inhibition rendered by said agent and at the same time acts to protect normal cells by inhibiting cell cycle progression.

32. The process according to claim 30 wherein therapeutic agent is further delivered when one or more cold stress proteins are expressed, said proteins initiating the release of mediators that stimulate a pro-inflammatory response.

33. The process according to claim 31 wherein said therapeutic agent is further delivered when one or more cold stress proteins are expressed, said proteins initiating the release of mediators that stimulate a pro-inflammatory response.

34. The process according to claim 30 wherein said cancerous disease inhibiting therapeutic agent is released from said microencapsulation dependant manner to correspond with at least one or more said cellular and molecular events associated with said thermal-related stress response.

35. The process according to claim 33 wherein said cancerous disease inhibiting therapeutic agent is released from said microencapsulation in a time dependant manner to correspond with at least one or more said cellular and molecular events associated with said thermal-related stress response.

36. The process according to claim 30 wherein said cancerous disease inhibiting therapeutic agent includes at least one cytotoxic drug and at least one immune stimulant or cytokine.

37. The process according to claim 35 wherein said cancerous disease inhibiting therapeutic agent includes at least one cytotoxic drug and at least one immune stimulant or cytokine.

38. The process according to claim 30 wherein said cancerous disease inhibiting therapeutic agent is 5-fluorouracil or paclitaxel.

39. The process according to claim 37 wherein said cancerous disease inhibiting therapeutic agent is 5-fluorouracil or paclitaxel.

40. The process according to claim 30 wherein said exposure of said tumor to said hypothermic treatment further includes at least one cryoprobe.

* * * * *